United States Patent [19]
Wozney et al.

[11] Patent Number: 5,366,875
[45] Date of Patent: * Nov. 22, 1994

[54] METHODS FOR PRODUCING BMP-7 PROTEINS

[75] Inventors: John M. Wozney, Hudson; Elizabeth A. Wang, Carlisle; Vicki A. Rosen, Brookline, all of Mass.

[73] Assignee: Genetics Institute, Inc., Cambridge, Mass.

[*] Notice: The portion of the term of this patent subsequent to Apr. 21, 2009 has been disclaimed.

[21] Appl. No.: 764,731

[22] Filed: Sep. 24, 1991

Related U.S. Application Data

[63] Continuation of Ser. No. 370,549, Jun. 23, 1989, abandoned, which is a continuation-in-part of Ser. No. 347,559, May 4, 1989, abandoned, and Ser. No. 329,610, Mar. 28, 1989, abandoned, each is a continuation-in-part of Ser. No. 179,100, Apr. 8, 1988, Pat. No. 5,013,649, Ser. No. 179,101, Apr. 8, 1988, and Ser. No. 179,197, Apr. 8, 1988, each is a continuation-in-part of Ser. No. 28,285, Mar. 20, 1987, abandoned, and Ser. No. 31,346, Mar. 26, 1987, Pat. No. 4,877,864, each is a continuation-in-part of Ser. No. 943,332, Dec. 17, 1986, abandoned, and Ser. No. 880,776, Jul. 1, 1986.

[51] Int. Cl.$^5$ .............. C12P 21/02; C12P 19/34; C12N 15/00; C12N 7/00; C12N 5/00; C07H 15/12; C07K 3/00

[52] U.S. Cl. .............. 435/69.1; 435/172.3; 435/235.1; 435/320.1; 435/240.1; 536/23.51; 536/23.5; 530/380; 935/9; 935/32; 935/34; 935/57; 935/62; 935/70

[58] Field of Search .............. 435/69.1, 91, 173.2, 435/235.1, 320.1, 240.1; 536/27; 530/350; 535/9, 32, 34, 57, 62, 70

[56] References Cited

U.S. PATENT DOCUMENTS

| | | | |
|---|---|---|---|
| 4,294,753 | 10/1981 | Urist | 530/395 |
| 4,399,216 | 8/1983 | Axel et al. | 435/6 |
| 4,434,094 | 2/1984 | Seyedin et al. | 530/416 |
| 4,455,256 | 6/1984 | Urist | 530/350 |
| 4,563,350 | 1/1986 | Nathan | 424/95 |
| 4,608,199 | 8/1986 | Caplan et al. | 530/414 |
| 4,627,982 | 12/1986 | Seyedin et al. | 424/95 |
| 4,681,763 | 7/1987 | Nathanson | 424/95 |
| 4,737,578 | 4/1988 | Evans | 530/350 |
| 4,761,471 | 8/1988 | Urist | 530/350 |
| 4,766,067 | 8/1988 | Biswas et al. | 435/69.1 |
| 4,774,228 | 9/1988 | Seyedin | 514/21 |
| 4,774,322 | 9/1988 | Seyedin | 530/353 |
| 4,789,732 | 12/1988 | Urist | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |
| 4,886,747 | 12/1989 | Derynck | 435/69.4 |
| 4,968,590 | 11/1990 | Kuberasampath et al. | 530/326 |
| 5,011,691 | 4/1991 | Oppermann | 424/423 |

FOREIGN PATENT DOCUMENTS

| | | | |
|---|---|---|---|
| 2017466 | 5/1990 | Canada | C12N 15/16 |
| 336760 | 6/1989 | European Pat. Off. | C07K 7/00 |
| 0416578A2 | 5/1990 | European Pat. Off. | C12N 15/12 |
| 0409472A1 | 11/1990 | European Pat. Off. | C12N 15/12 |
| WO89/09787 | 10/1989 | WIPO | C07K 13/00 |
| WO89/09788 | 10/1989 | WIPO | C07K 13/00 |
| WO90/03733 | 4/1990 | WIPO | A01N 63/02 |
| WO91/02744 | 3/1991 | WIPO | C07K 15/06 |
| WO91/05802 | 5/1991 | WIPO | C07K 15/00 |

OTHER PUBLICATIONS

Celeste et al Proc. Natl Acad Sci USA vol. 87 pp. 9843–9847 (1982).
Urist, et al, *Science*, 220: 680–686 (1983).
Sampath, et al, *Proc. Natl. Acad. Sci.*, 84: 7109–7113 (1987).
Ozkaynak et al *EMBO* 9: 2085–2093 (1990).

*Primary Examiner*—Joan Ellis
*Attorney, Agent, or Firm*—Ellen J. Kapinos; Thomas J. DesRosier

[57] ABSTRACT

Purified BMP-7 proteins and processes for producing them are disclosed. The proteins may be used in the treatment of bone and/or cartilage defects and in wound healing and related tissue repair.

8 Claims, 8 Drawing Sheets

FIGURE 1

```
1   TCTAGAGGTGAGAGCAGCCAACAAGAGAAAAAAATCAAAACCGCAATAAATCCGGCTCTCAT   61
    LeuGluValArgAlaAlaAsnLysArgLysAsnGlnAsnArgAsnLysSerGlySerHis
         (1)                                          (15)

2   CAGGACTCCTCTAGAATGTCCAGTGTTGGAGATTATAACACCAGTGAACAAAAACAAGCC   121
     GlnAspSerSerArgMetSerSerValGlyAspTyrAsnThrSerGluGlnLysGlnAla
              (23)

122 TGTAAAAAGCATGAACTCTATGTGAGTTTCCGGGATCTGGGATGGCAGGACTGGATTATA   181
    CysLysLysHisGluLeuTyrValSerPheArgAspLeuGlyTrpGlnAspTrpIleIle
              (42)

182 GCACCAGAAGGATATGCTGCATTTTATTGTGATGGAGAATGTTCTTTTCCACTCAATGCC   241
    AlaProGluGlyTyrAlaAlaPheTyrCysAspGlyGluCysSerPheProLeuAsnAla

242 CATATGAATGCCACCAATCATGCCATAGTTCAGACTCTGGTTCACCTGATGTTTCCTGAC   301
    HisMetAsnAlaThrAsnHisAlaIleValGlnThrLeuValHisLeuMetPheProAsp

302 CACGTACCAAAGCCTTGCTGCGCGACAAACAAACTAAATGCCATCTCTGTGTTGTACTTT   361
    HisValProLysProCysCysAlaThrAsnLysLeuAsnAlaIleSerValLeuTyrPhe

362 GATGACAGCTCCAATGTCATTTTGAAAAAGTACAGAAATATGGTCGTGCGTTCGTGTGGT   421
    AspAspSerSerAsnValIleLeuLysLysTyrArgAsnMetValValArgSerCysGly

422 TGCCACTAATAGTGCATAATAATGGTAATAAGAAAAAAGATCTGTATGGAGGTTTATGA   481
    CysHisEnd
       (140)

481    CTACAATAAAAAATATCTTTCGGATAAAAGGGGAATTTAATAAAATTAGTCTGGCTCATT   540

541    TCATCTCTGTAACCTATGTACAAGAGCATGTATATAGT                       578
```

FIGURE 2

```
              9            18             27            36            45            54
CTG CTG GGC ACG CGT GCT GTG TGG GCC TCA GAG GCG GGC TGG CTG GAG TTT GAC
Leu Leu Gly Thr Arg Ala Val Trp Ala Ser Glu Ala Gly Trp Leu Glu Phe Asp
(1)

63            72             81            90            99           108
ATC ACG GCC ACC AGC AAC CTG TGG GTC CTG ACT CCG CAG CAC AAC ATG GGG CTG
Ile Thr Ala Thr Ser Asn Leu Trp Val Leu Thr Pro Gln His Asn MET Gly Leu 117           126            135           144           153           162
CAG CTG AGC GTG GTC ACG CGT GAT GGG CTC AGC ATC AGC CCT GGG GCC GCG GGC
Gln Leu Ser Val Val Thr Arg Asp Gly Leu Ser Ile Ser Pro Gly Ala Ala Gly 171           180            189           198           207           216
CTG GTG GGC AGG GAC GGC CCC TAC GAC AAG CAG CCC TTC ATG GTG GCC TTC TTC
Leu Val Gly Arg Asp Gly Pro Tyr Asp Lys Gln Pro Phe MET Val Ala Phe Phe 225           234            243           252           261           270
AAG GCC AGT GAG GTC CAC GTG CGC AGT GCC CGG TCG GCC CCC GGG CGG CGC CGG
Lys Ala Ser Glu Val His Val Arg Ser Ala Arg Ser Ala Pro Gly Arg Arg Arg 279           288            297           306           315           324
CAG CAG GCC CGG AAC CGC TCC ACC CCG GCC CAG GAC GTG TCG CGG GCC TCC AGC
Gln Gln Ala Arg Asn Arg Ser Thr Pro Ala Gln Asp Val Ser Arg Ala Ser Ser 333           342            351           360           369           378
GCC TCA GAC TAC AAC AGC AGC GAG CTG AAG ACG GCC TGC CGG AAG CAT GAG CTC
Ala Ser Asp Tyr Asn Ser Ser Glu Leu Lys Thr Ala Cys Arg Lys His Glu Leu 387           396            405           414           423           432
TAC GTG AGC TTC CAG GAC CTG GGG TGG CAG GAC TGG ATC ATT GCC CCC AAG GGC
Tyr Val Ser Phe Gln Asp Leu Gly Trp Gln Asp Trp Ile Ile Ala Pro Lys Gly 441           450            459           468           477           486
TAC GCT GCC AAC TAC TGT GAC GGA GAA TGT TCG TTC CCT CTC AAC GCA CAC ATG
Tyr Ala Ala Asn Tyr Cys Asp Gly Glu Cys Ser Phe Pro Leu Asn Ala His MET 495           504            513           522           531           540
AAC GCT ACC AAC CAT GCC ATC GTG CAG ACC CTG GTT CAC CTC ATG AAC CCC GAG
Asn Ala Thr Asn His Ala Ile Val Gln Thr Leu Val His Leu MET Asn Pro Glu 549           558            567           576           585           594
TAC GTC CCC AAA CCG TGC TGC GCG CCC ACG AAA CTG AAC GCC ATC TCG GTG CTC
Tyr Val Pro Lys Pro Cys Cys Ala Pro Thr Lys Leu Asn Ala Ile Ser Val Leu 603           612            621           630           639           648
TAC TTC GAC GAC AAC TCC AAT GTC ATC CTG AAG AAG TAC CGG AAC ATG GTC GTA
Tyr Phe Asp Asp Asn Ser Asn Val Ile Leu Lys Lys Tyr Arg Asn MET Val Val
```

FIGURE 2A

```
    657         666         676         686         696         706
CGA GCG TGT GGG T GGC CAC TGACTCGGGG TGAGTGGCTG GGGACGCTGT GCACACACTG
Arg Ala Cys Gly Cys His
              (222)

716        726        736        746        756        766        776
CCTGGACTCC TGGATCACGT CCGCCCTAAG CCCACAGAGG CCCCCGGGAC ACAGGAGGAG ACCCCGAGGC 786        796        806        816        826        836        846
CACCTTCGGC TGGCGTTGGC CTTTCCGCCC AACGCAGACC CGAAGGGACC CTGTCCGCCC CTTGCTCACA 856        866        876        886
CCGTGAGCGT TGTGAGTAGC CATCGGGCTC TAGGAAGCAG CACTCGAG
```

FIGURE 3

```
             9              18              27              36              45              54
CAA CAG AGT CGT AAT CGC TCT ACC CAG TCC CAG GAC GTG GCG CGG GTC TCC AGT
Gln Gln Ser Arg Asn Arg Ser Thr Gln Ser Gln Asp Val Ala Arg Val Ser Ser
(1)
            63              72              81              90              99             108
GCT TCA GAT TAC AAC AGC AGT GAA TTG AAA ACA GCC TGC AGG AAG CAT GAG CTG
Ala Ser Asp Tyr Asn Ser Ser Glu Leu Lys Thr Ala Cys Arg Lys His Glu Leu 117             126             135             144             153             162
TAT GTG AGT TTC CAA GAC CTG GGA TGG CAG GAC TGG ATC ATT GCA CCC AAG GGC
Tyr Val Ser Phe Gln Asp Leu Gly Trp Gln Asp Trp Ile Ile Ala Pro Lys Gly 171             180             189             198             207             216
TAT GCT GCC AAT TAC TGT GAT GGA GAA TGC TCC TTC CCA CTC AAC GCA CAC ATG
Tyr Ala Ala Asn Tyr Cys Asp Gly Glu Cys Ser Phe Pro Leu Asn Ala His MET 225             234             243             252             261             270
AAT GCA ACC AAC CAC GCG ATT GTG CAG ACC TTG GTT CAC CTT ATG AAC CCC GAG
Asn Ala Thr Asn His Ala Ile Val Gln Thr Leu Val His Leu MET Asn Pro Glu 279             288             297             306             315             324
TAT GTC CCC AAA CCG TGC TGT GCG CCA ACT AAG CTA AAT GCC ATC TCG GTT CTT
Tyr Val Pro Lys Pro Cys Cys Ala Pro Thr Lys Leu Asn Ala Ile Ser Val Leu 333             342             351             360             369             378
TAC TTT GAT GAC AAC TCC AAT GTC ATT CTG AAA AAA TAC AGG AAT ATG GTT GTA
Tyr Phe Asp Asp Asn Ser Asn Val Ile Leu Lys Lys Tyr Arg Asn MET Val Val 387             396
AGA GCT TGT GGA TGC CAC TAA
Arg Ala Cys Gly Cys His
```

FIGURE 4

```
         9           18          27          36          45          54
CAG GCC TGT AAG AAG CAC GAG CTG TAT GTC AGC TTC CGA GAC CTG GGC TGG CAG
Gln Ala Cys Lys Lys His Glu Leu Tyr Val Ser Phe Arg Asp Leu Gly Trp Gln
(1)

63          72          81          90          99         108
GAC TGG ATC ATC GCG CCT GAA GGC TAC GCC GCC TAC TAC TGT GAG GGG GAG TGT
Asp Trp Ile Ile Ala Pro Glu Gly Tyr Ala Ala Tyr Tyr Cys Glu Gly Glu Cys 117         126         135         144         153         162
GCC TTC CCT CTG AAC TCC TAC ATG AAC GCC ACC AAC CAC GCC ATC GTG CAG ACG
Ala Phe Pro Leu Asn Ser Tyr MET Asn Ala Thr Asn His Ala Ile Val Gln Thr 171         180         189         198         207         216
CTG GTC CAC TTC ATC AAC CCG GAA ACG GTG CCC AAG CCC TGC TGT GCG CCC ACG
Leu Val His Phe Ile Asn Pro Glu Thr Val Pro Lys Pro Cys Cys Ala Pro Thr 225         234         243         252         261         270
CAG CTC AAT GCC ATC TCC GTC CTC TAC TTC GAT GAC AGC TCC AAC GTC ATC CTG
Gln Leu Asn Ala Ile Ser Val Leu Tyr Phe Asp Asp Ser Ser Asn Val Ile Leu 279         288         297         306         315
AAG AAA TAC AGA AAC ATG GTG GTC CGG GCC TGT GGC TGC CAC TAG
Lys Lys Tyr Arg Asn MET Val Val Arg Ala Cys Gly Cys His
                                                    (104)
```

FIGURE 5

```
  1
AGC CTG GAC AAC GAG GTG CAC TCG AGC TTC ATC CAC CGG CGC CTC
Ser Leu Asp Asn Glu Val His Ser Ser Phe Ile His Arg Arg Leu
-260
 48
CGC AGC CAG GAG CGG CGG GAG ATG CAG CGC GAG ATC CTC TCC ATT
Arg Ser Gln Glu Arg Arg Glu MET Gln Arg Glu Ile Leu Ser Ile

96
TTG GGC TTG CCC CAC CGC CCG CGC CCG CAC CTC CAG GGC AAG CAC
Leu Gly Leu Pro His Arg Pro Arg Pro His Leu Gln Gly Lys His

144
AAC TCG GCA CCC ATG TTC ATG CTG GAC CTG TAC AAC GCC ATG GCG
Asn Ser Ala Pro MET Phe MET Leu Asp Leu Tyr Asn Ala MET Ala

192
GTG GAG GAG GGC GGC GGG CCC GGC GGC CAG GGC TTC TCC TAC CCC
Val Glu Glu Gly Gly Gly Pro Gly Gly Gln Gly Phe Ser Tyr Pro

240
TAC AAG GCC GTC TTC AGT ACC CAG GGC CCC CCT CTG GCC AGC CTG
Tyr Lys Ala Val Phe Ser Thr Gln Gly Pro Pro Leu Ala Ser Leu

288
CAA GAT AGC CAT TTC CTC ACC GAC GCC GAC ATG GTC ATG AGC TTC
Gln Asp Ser His Phe Leu Thr Asp Ala Asp MET Val MET Ser Phe

336
GTC AAC CTC GTG GAA CAT GAC AAG GAA TTC TTC CAC CCA CGC TAC
Val Asn Leu Val Glu His Asp Lys Glu Phe Phe His Pro Arg Tyr

384
CAC CAT CGA GAG TTC CGG TTT GAT CTT TCC AAG ATC CCA GAA GGG
His His Arg Glu Phe Arg Phe Asp Leu Ser Lys Ile Pro Glu Gly

432
GAA GCT GTC ACG GCA GCC GAA TTC CGG ATC TAC AAG GAC TAC ATC
Glu Ala Val Thr Ala Ala Glu Phe Arg Ile Tyr Lys Asp Tyr Ile

480
CGG GAA CGC TTC GAC AAT GAG ACG TTC CGG ATC AGC GTT TAT CAG
Arg Glu Arg Phe Asp Asn Glu Thr Phe Arg Ile Ser Val Tyr Gln

528
GTG CTC CAG GAG CAC TTG GGC AGG GAA TCG GAT CTC TTC CTG CTC
Val Leu Gln Glu His Leu Gly Arg Glu Ser Asp Leu Phe Leu Leu
```

FIGURE 5A

```
                                                576
GAC AGC CGT ACC CTC TGG GCC TCG GAG GAG GGC TGG CTG GTG TTT
Asp Ser Arg Thr Leu Trp Ala Ser Glu Glu Gly Trp Leu Val Phe

624
GAC ATC ACA GCC ACC AGC AAC CAC TGG GTG GTC AAT CCG CGG CAC
Asp Ile Thr Ala Thr Ser Asn His Trp Val Val Asn Pro Arg His

672
AAC CTG GGC CTG CAG CTC TCG GTG GAG ACG CTG GAT GGG CAG AGC
Asn Leu Gly Leu Gln Leu Ser Val Glu Thr Leu Asp Gly Gln Ser

720
ATC AAC CCC AAG TTG GCG GGC CTG ATT GGG CGG CAC GGG CCC CAG
Ile Asn Pro Lys Leu Ala Gly Leu Ile Gly Arg His Gly Pro Gln

AAC AAG CAG CCC TTC ATG GTG GCT TTC TTC AAG GCC ACG GAG GTC
Asn Lys Gln Pro Phe MET Val Ala Phe Phe Lys Ala Thr Glu Val

768
CAC TTC CGC AGC ATC CGG TCC ACG GGG AGC AAA CAG CGC AGC CAG
His Phe Arg Ser Ile Arg Ser Thr Gly Ser Lys Gln Arg Ser Gln

816
AAC CGC TCC AAG ACG CCC AAG AAC CAG GAA GCC CTG CGG ATG GCC
Asn Arg Ser Lys Thr Pro Lys Asn Gln Glu Ala Leu Arg MET Ala
                             (18)              (23)
        864
AAC GTG GCA GAG AAC AGC AGC AGC GAC CAG AGG CAG GCC TGT AAG
Asn Val Ala Glu Asn Ser Ser Ser Asp Gln Arg Gln Ala Cys Lys
                                                (37)
        912
AAG CAC GAG CTG TAT GTC AGC TTC CGA GAC CTG GGC TGG CAG GAC
Lys His Glu Leu Tyr Val Ser Phe Arg Asp Leu Gly Trp Gln Asp
    (42)                    (48)
                960
TGG ATC ATC GCG CCT GAA GGC TAC GCC GCC TAC TAC TGT GAG GGG
Trp Ile Ile Ala Pro Glu Gly Tyr Ala Ala Tyr Tyr Cys Glu Gly

1008
GAG TGT GCC TTC CCT CTG AAC TCC TAC ATG AAC GCC ACC AAC CAC
Glu Cys Ala Phe Pro Leu Asn Ser Tyr MET Asn Ala Thr Asn His

1056
GCC ATC GTG CAG ACG CTG GTC CAC TTC ATC AAC CCG GAA ACG GTG
Ala Ile Val Gln Thr Leu Val His Phe Ile Asn Pro Ile Ser Val
```

FIGURE 5B

```
                    1104
CCC AAG CCC TGC TGT GCG CCC ACG CAG CTC AAT GCC ATC TCC GTC
Pro Lys Pro Cys Cys Ala Pro Thr Gln Leu Asn Ala Ile Ser Val

1152
CTC TAC TTC GAT GAC AGC TCC AAC GTC ATC CTG AAG AAA TAC AGA
Leu Tyr Phe Asp Asp Ser Ser Asn Val Ile Leu Lys Lys Tyr Arg

1200
AAC ATG GTG GTC CGG GCC TGT GGC TGC CAC TAGCTCCTCC
Asn MET Val Val Arg Ala Cys Gly Cys His
                                  (140)

GAGAATTCAG ACCCTTTGGG GCCAAGTTTT TCTGGATCCT CCATTGCTC
```

METHODS FOR PRODUCING BMP-7 PROTEINS

This application is a continuation of U.S. Ser. No. 370,549 filed Jun. 23, 1989, now abandoned, which is a continuation-in-part of U.S. Ser. Nos. 347,559 filed May 4, 1989, now abandoned, and 329,610 filed Mar. 28, 1989, now abandoned, which are continuations-in-part of U.S. Ser. Nos. 179,100, filed Apr. 8, 1988 now U.S. Pat. Nos. 5,013,649; 179,101filed Apr. 8, 1988; and 179,197 filed Apr. 8, 1988, which are continuations-in-part of U.S. Ser. Nos 028,285 filed Mar. 20, 1987, now abandoned and 031,346 filed Mar. 26, 1987, now U.S. Pat. No. 4,877,864 which are continuations-in-part of U.S. Ser. Nos. 943,332 filed Dec. 17, 1986, now abandoned, and 880,776 filed Jul. 1, 1986, now abandoned.

The present invention relates to a family of purified proteins, termed BMP-7 proteins (wherein BMP is bone morphogenic protein), which exhibit the ability to induce cartilage and/or bone formation and processes for obtaining them. These proteins may be used to induce bone and/or cartilage formation and in wound healing and tissue repair.

The invention provides human BMP-7 proteins, substantially free from other proteins with which they are co-produced, characterized by containing the amino acid sequence set forth in FIG. 4 (SEQ ID NO: 8) from amino acid #1 to amino acid #104 encoded for by the DNA sequence of FIG. 4 (SEQ ID NO: 7) from nucleotide #1 to nucleotide #312. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein reveals a region of approximately 14,000–20,000 daltons. It is contemplated that these proteins are capable of stimulating promoting, or otherwise inducing cartilage and/or bone formation.

These human BMP-7 proteins of the invention may be produced by culturing a cell transformed with a DNA sequence containing the nucleotide sequence the same or substantially the same as shown in FIG. 4 from nucleotide #1 to nucleotide #312, recovering and purifying from the culture medium a protein containing the amino acid sequence the same or substantially the same as shown in FIG. 4 from amino acid #1 to amino acid #104.

In another embodiment, the DNA sequence of FIG. 5 (SEQ. ID NO: 9) from nucleotide #1 to nucleotide #1200 encodes the BMP-7 amino acid sequence set forth in FIG. 5 (SEQ ID NO: 10) from amino acid #-260(Ser) to amino acid #140(His). These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein reveals a region of approximately 14,000–20,000 daltons. It is contemplated that these proteins are capable of stimulating promoting, or otherwise inducing cartilage and/or bone formation.

These BMP-7 proteins may be produced by culturing a cell transformed with a DNA sequence containing the nucleotide sequence the same or substantially the same as shown in FIG. 5 from nucleotide #1 to nucleotide #1200, recovering and purifying from the culture medium a BMP-7.

The invention further provides a method wherein the proteins described above are utilized for obtaining related human protein/s or other mammalian cartilage and/or bone growth protein/s. Such methods are known to those skilled in the art of genetic engineering. One method for obtaining such proteins involves utilizing the human BMP-7 coding sequence as a probe for screening genomic and/or cDNA libraries to isolate the genomic and/or cDNA sequence.

These proteins are produced by culturing a cell transformed with the DNA identified as in the method described above which DNA hybridizes under stringent conditions to the nucleotide sequence substantially as shown in FIG. 4 (SEQ ID NO: 7) from nucleotide #1 to nucleotide #312 or nucleotide #1 to #1200 of FIG. 5 (SEQ ID NO: 9) which encodes a protein exhibiting cartilage and/or bone formation activity and recovering and purifying from the culture medium a protein substantially free from other proteinaceous with which it is co-produced.

The proteins of the invention may be further characterized by the ability to demonstrate cartilage and/or bone formation activity in the rat bone formation assay described below. It is further contemplated that the proteins of the invention demonstrate activity in this rat bone formation assay at a concentration of $0.5\mu$–100 $\mu$g/gram of bone. It is further contemplated that these proteins demonstrate activity in this assay at a concentration of 1 $\mu$g–50 $\mu$g/gram bone. More particularly, it is contemplated these proteins may be characterized by the ability of 1 $\mu$g of the protein to score at least +2 in the rat bone formation assay.

Another aspect of the invention provides pharmaceutical compositions containing a therapeutically effective amount of a protein of the invention in a pharmaceutically acceptable vehicle or carrier. The compositions of the invention may be used to induce bone and/or cartilage formation. These compositions may also be used for wound healing and tissue repair. Further compositions of the invention may include in addition to a BMP-7 protein of the present invention at least one other therapeutically useful agent such as the proteins designated BMP-1, BMP-2A and -2B, BMP-3, BMP-5, and BMP-6 disclosed respectively in co-owned U.S. patent application Ser. Nos. 179,101, 179,100, and 179,197, 370,547 filed Jun. 22, 1989, and 370,544 filed Jun. 22, 1989. Other therapeutically useful agents include growth factors such as epidermal growth factor (EGF), fibroblast growth factor (FGF), and transforming growth factors (TGF-$\alpha$ and TGF-$\beta$). The compositions of the invention may also include an appropriate matrix, for instance, for supporting the composition and/or providing a surface for bone and/or cartilage growth.

The compositions may be employed in methods for treating a number of bone and/or cartilage defects, and periodontal disease. They may also be employed in methods for treating various types of wounds and in tissue repair. These methods, according to the invention, entail administering to a patient needing such bone and/or cartilage formation, wound healing or tissue repair, a therapeutically effective amount of a protein of the invention. These methods may also entail the administration of a protein of the invention in conjunction with at least one of the "BMP" proteins disclosed in the co-owned applications described above. In addition, these methods may also include the administration of a protein of the invention with other growth factors including EGF, FGF, TGF-$\alpha$, and TGF-$\beta$.

Still a further aspect of the invention are DNA sequences coding for expression of a protein of the invention. Such sequences include the sequence of nucleotides in a 5' to 3' direction illustrated in FIGS. 4 (SEQ ID NO: 7) or 5 (SEQ ID NO: 9) or DNA sequences which hybridize under stringent conditions with the DNA sequences of FIGS. 4 and 5 and encode a protein demonstrating ability to induce cartilage and/or bone formation in the rat bone formation assay described below. It is contemplated that these proteins demonstrate activity in this assay at a concentration of 0.5 μg–100 μg/gram of bone. It is further contemplated that the proteins demonstrate activity in this assay at a concentration of 1 μg–50 μg/gram bone. More particularly, it is contemplated that these proteins demonstrate the ability of 1 μg of the protein to score at least +2 in the rat bone formation assay. Finally, allelic or other variations of the sequences of FIGS. 4 and 5 whether such nucleotide changes result in changes in the peptide sequence or not, are also included in the present invention.

A further aspect of the invention provides a vector containing a DNA sequence as described above in operative association with an expression control sequence therefor. These vectors may be employed in a novel process for producing a protein of the invention in which a cell line transformed with a DNA sequence directing expression of a protein of the invention in operative association with an expression control sequence therefor, is cultured in a suitable culture medium and a protein of the invention is isolated and purified therefrom. This claimed process may employ a number of known cells, both prokaryotic and eukaryotic, as host cells for expression of the polypeptide.

Other aspects and advantages of the present invention will be apparent upon consideration of the following detailed description and preferred embodiments thereof.

BRIEF DESCRIPTION OF THE DRAWING

FIG. 1 comprises DNA sequence and derived amino acid sequence of bovine BMP-5.

FIGS. 2 and 2A comprise DNA sequence and derived amino acid sequence of bovine BMP-6.

FIG. 3 comprises DNA sequence and derived amino acid sequence of human BMP-6 from lambda U2-7 ATCC #68021.

FIG. 4 comprises partial DNA and amino acid sequence of lambda U2-5 ATCC #68020 encoding BMP-7.

FIGS. 5, 5A–B comprise DNA and amino acid sequence of lambda U2-5 ATCC #68020 encoding BMP-7.

DETAILED DESCRIPTION OF THE INVENTION

A purified BMP-7 human cartilage/bone protein of the present invention is produced by culturing a host cell transformed with a DNA sequence comprising the DNA sequence as shown in FIG. 4 (SEQ ID NO: 7) from nucleotide #1 to nucleotide #312 or substantially homologous sequences operatively linked to a heterologous regulatory control sequence and recovering, isolating and purifying from the culture medium a protein containing the amino acid sequence as shown in FIG. 4 (SEQ ID NO: 8) from amino acid #1 to amino acid #104 or a substantially homologous sequence.

In another embodiment, a purified BMP-7 human cartilage/bone protein of the present invention is produced by culturing a host cell transformed with a DNA sequence comprising the DNA sequence as shown in FIG. 5 (SEQ ID NO: 9) from nucleotide #1 to nucleotide #1200 or substantially homologous sequences operatively linked to a heterologous regulatory control sequence and recovering, isolating and purifying from the culture medium a BMP-7 protein.

These proteins may be further characterized by the ability to demonstrate cartilage and/or bone formation activity in the rat bone formation assay as described in Example III. It is further contemplated that these proteins demonstrate activity in the assay at a concentration of 0.5 μg–100 μg/gram of bone formed. It is further contemplated that these proteins demonstrate activity in this assay at a concentration of 1 μg–50 μg/gram bone. The proteins may be further characterized by the ability of 1 μg to score at least +2 in this assay.

The proteins provided herein also include factors encoded by the sequences similar to those of FIGS. 4 and 5, but into which modifications are naturally provided (e.g. allelic variations in the nucleotide sequence which may result in amino acid changes in the polypeptide) or deliberately engineered. Similarly, synthetic polypeptides which wholly or partially duplicate continuous sequences of the amino acid residues of FIGS. 4 and 5 (SEQ ID NO: 8 and 10) are encompassed by the invention. These sequences, by virtue of sharing primary, secondary, or tertiary structural and conformational characteristics with other cartilage/bone proteins of the invention may possess bone and/or cartilage growth factor biological properties in common therewith. Thus, they may be employed as biologically active substitutes for naturally-occurring proteins in therapeutic processes.

Other specific mutations of the sequences of the proteins of the invention described herein involve modifications of the glycosylation sites. The absence of glycosylation or only partial glycosylation results from amino acid substitution or deletion at the asparagine-linked glycosylation recognition sites present in the sequences of the proteins of the invention, for example, as shown in FIGS. 4 and 5. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence.

The present invention also encompasses the novel DNA sequences, free of association with DNA sequences encoding other proteinaceous materials, and coding on expression for the proteins of the invention. These DNA sequences include those depicted in FIGS. 4 and 5 (SEQ ID NO: 7 and 9) in a 5' to 3' direction. Further included are those sequences which hybridize under stringent hybridization conditions [see, T. Maniatis et al, *Molecular Cloning (A Laboratory Manual)*, Cold Spring Harbor Laboratory (1982), pages 387 to 389] to the DNA sequences of FIG. 4 or FIG. 5 and demonstrate cartilage and/or bone formation activity in the rat bone formation assay. An example of one such stringent hybridization condition is hybridization at 4×SSC at 65° C., followed by a washing in 0.1×SCC at 65° C. for an hour. Alternatively, an examplary stringent hybridization condition is in 50% formamide, 4×SCC at 42° C.

Similarly, DNA sequences which encode proteins similar to the protein encoded by the sequence of FIG. 4 or FIG. 5, but which differ in codon sequence due to the degeneracies of the genetic code or allelic variations (naturally-occurring base changes in the species population which may or may not result in an amino acid change) also encode the proteins of the invention described herein. Variations in the DNA sequences of FIG. 4 or FIG. 5 which are caused by point mutations or by induced modifications (including insertion, deletion, and substitution) to enhance the activity, half-life or production of the polypeptides encoded thereby are also encompassed in the invention.

In a further aspect, the invention provides a method for obtaining related human proteins or other mammalian BMP-7 proteins. One method for obtaining such proteins entails, for instance, utilizing the human BMP-7 coding sequence disclosed herein to probe a human genomic library using standard techniques for the human gene or fragments thereof. Sequences thus thus identified may also be used as probes to identify a human cell line or tissue which synthesizes the analogous cartilage/bone protein. A cDNA library is synthesized and screened with probes derived from the human or bovine coding sequences. The human sequence thus identified is transformed into a host cell, the host cell is cultured and the protein recovered, isolated and purified from the culture medium. The purified protein is predicted to exhibit cartilage and/or bone formation activity in the rat bone formation assay of Example III.

Another aspect of the present invention provides a novel method for producing the proteins of the invention. The method of the present invention involves culturing a suitable cell line, which has been transformed with a DNA sequence coding for expression of a protein of the invention, under the control of known regulatory sequences. The transformed cells are cultured and the BMP-7 proteins expressed thereby are recovered and purified from the culture medium using purification techniques known to those skilled in the art.

Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of the proteins of the invention. Preferably the vectors contain the full novel DNA sequences described above which code for the novel BMP-7 proteins of the invention. Additionally the vectors also contain appropriate expression control sequences permitting expression of the protein sequences. Alternatively, vectors incorporating modified sequences as described above are also embodiments of the present invention and useful in the production of the proteins of the invention. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to those skilled in the art and may be selected depending upon the selected host cells. Such selection is routine and does not form part of the present invention. Host cells transformed with such vectors and progeny thereof for use in producing BMP-7 proteins are also provided by the invention.

A protein of the present invention, which induces cartilage and/or bone formation in circumstances where bone and/or cartilage is not normally formed, has application in the healing of bone fractures and cartilage defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A protein of the invention may be used in the treatment of periodontal disease, and in other tooth repair processes. Such agents may provide an environment to attract bone-forming cells, stimulate growth of bone-forming cells or induce differentiation of progenitors of bone-forming cells. A variety of osteogenic, cartilage-inducing and bone inducing factors have been described. See, e.g. European patent applications 148,155 and 169,016 for discussions thereof.

The proteins of the invention may also be used in wound healing and related tissue repair. The types of wounds include, but are not limited to burns, incisions and ulcers. (See, e.g. PCT Publication W084/01106 for discussion of wound healing and related tissue repair).

A further aspect of the invention is a therapeutic method and composition for repairing fractures and other conditions related to bone and/or cartilage defects or periodontal diseases. In addition, the invention comprises therapeutic methods and compositions for wound healing and tissue repair. Such compositions comprise a therapeutically effective amount of at least one of the proteins of the invention in admixture with a pharmaceutically acceptable vehicle, carrier or matrix. It is expected that the proteins of the invention may act in concert with or perhaps synergistically with one another or with other related proteins and growth factors. Therapeutic methods and compositions of the invention therefore comprise one or more of the proteins of the present invention. Further therapeutic methods and compositions of the invention therefore comprise a therapeutic amount of at least one protein of the invention with a therapeutic amount of at least one of the other "BMP" proteins disclosed in co-owned and co-pending U.S. applications described above. Such methods and compositions of the invention may comprise proteins of the invention or portions thereof in combination with the above-mentioned "BMP" proteins or portions thereof. Such combination may comprise individual molecules from each of the proteins or heteromolecules formed by portions of the respective proteins. For example, a method and composition of the invention may comprise a protein of the invention or a portion thereof linked with a portion of a "BMP" protein to form a heteromolecule.

Further therapeutic methods and compositions of the invention comprise the proteins of the invention or portions thereof in combination with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-α and TGF-β), and insulin-like growth factor (IGF). Portions of these agents may also be used in compositions of the invention.

The preparation and formulation of such physiologically acceptable protein compositions, having due regard to pH, isotonicity, stability and the like, is within the skill of the art. The therapeutic compositions are also presently valuable for veterinary applications due to the apparent lack of species specificity in cartilage and bone growth factor proteins. Domestic animals and thoroughbred horses in addition to humans are desired patients for such treatment with the proteins of the present invention.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of cartilage and/or bone or tissue damage. Topical administration may be suitable for wound healing and tissue repair. Preferably for bone and/or cartilage formation, the composition would include a matrix capable of delivering the BMP-7 proteins of the invention to the site of bone and/or cartilage damage, providing a structure for the developing bone and cartilage and optimally capable of being resorbed into the body. Such matrices may be formed of materials presently in use for other implanted medical applications.

The choice of matrix material is based on biocompatibility, biodegradability, mechanical properties, cosmetic appearance and interface properties. The particular application of the compositions of the invention will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the proteins of the invention. Factors which may modify the action of the proteins of the invention include the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the type or types of bone and/or cartilage proteins present in the composition. The addition of other known growth factors, such as EGF, PDGF, TGF-α, TGF-β, and IGF-I to the final composition, may also effect the dosage.

Progress can be monitored by periodic assessment of cartilage and/or bone growth and/or repair. The progress can be monitored, for example, using x-rays, histomorphometric determinations and tetracycline labeling.

The following examples illustrate practice of the present invention in recovering and characterizing bovine cartilage and/or bone proteins of the invention and employing these proteins to recover the corresponding human protein or proteins and in expressing the proteins via recombinant techniques.

Isolation of Bovine Cartilage/Bone Inductive Protein

Ground bovine bone powder (20–120 mesh, Helitrex) is prepared according to the procedures of M. R. Urist et al., *Proc. Natl Acad. Sci USA*, 70:3511 (1973) with elimination of some extraction steps as identified below. Ten kgs of the ground powder is demineralized in successive changes of 0.6N HCl at 4° C. over a 48 hour period with vigorous stirring. The resulting suspension is extracted for 16 hours at 4° C. with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, 1 mM iodoacetamide, 1 mM phenylmethylsulfonyl fluorine as described in *Clin. Orthop. Rel. Res.*, 171:213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mM Tris, 0.1M NaCl, 6M urea (pH7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath-Reddi assay (described in Example III below) desorbed from the column by 50 mM NaAc, 0.25 mM NaCl, 6M urea (pH 4.6). The protein from this step elution is concentrated 20- to 40-fold, then diluted 5 times with 80 mM $KPO_4$, 6M urea (pH6.0). The pH of the solution is adjusted to 6.0 with 500 mM $K_2HPO_4$.

The sample is applied to an hydroxylapatite column (LKB) equilibrated in 80 mM KPO$_4$, 6M urea (pH6.0) and all unbound protein is removed by washing the column with the same buffer. Protein having bone and-/or cartilage formation activity is eluted with 100 mM KPO$_4$ (pH7.4) and 6M urea.

The protein is concentrated approximately 10 times, and solid NaCl added to a final concentration of 0.15M. This material is applied to a heparin-Sepharose column equilibrated in 50 mM KPO$_4$, 150 mM NaCl, 6M urea (pH7.4). After extensive washing of the column with starting buffer, a protein with bone and/or cartilage inductive activity is eluted by 50 mM KPO$_4$, 700 mM NaCl, 6M urea (pH7.4). This fraction is concentrated to a minimum volume, and 0.4 ml aliquots are applied to Superose 6 and Superose 12 columns connected in series, equilibrated with 4M GuCl, 20 mM Tris (pH7.2) and the columns developed at a flow rate of 0.25 ml/min. The protein demonstrating bone and/or cartilage inductive activity corresponds to an approximate 30,000 dalton protein.

The above fractions from the superose columns are pooled, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). Active bone and/or cartilage formation fractions are pooled. The active material is further fractionated on a MonoQ column. The protein is dialyzed against 6M urea, 25 mM diethanolamine, pH 8.6 and then applied to a 0.5 by 5 cm MonoQ column (Pharmacia) which is developed with a gradient of 6M urea, 25 mM diethanolamine, pH 8.6 and 0.5M NaCl, 6M urea, 25 mM diethanolamine, pH 8.6. Fractions are brought to pH3.0 with 10% trifluoroacetic acid (TFA). The material is applied to a 0.46×25 cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active material is eluted at approximately 40–44% acetonitrile. Fractions were assayed for cartilage and-/or bone formation activity.

Aliquots of the appropriate fractions are iodinated by one of the following methods: P. J. McConahey et al, *Int. Arch. Allergy*, 29:185–189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis.

EXAMPLE II

Characterization of Bovine Cartilage/Bone Inductive Factor

A. Molecular Weight

Approximately 5 µg protein from Example I in 6M urea, 25 mM diethanolamine, pH 8.6, approximately 0.3M NaCl is made 0.1% with respect to SDS and dialyzed against 50 mM tris/HCl 0.1% SDS pH 7.5 for 16 hrs. The dialyzed material is then electrophoretically concentrated against a dialysis membrane [Hunkapillar et al *Meth. Enzymol.* 91:227–236 (1983)] with a small amount of I 125 labelled counterpart. This material (volume approximately 100 µl) is loaded onto a 12% polyacrylamide gel and subjected to SDS-PAGE [Laemmli, U. K. *Nature*, 227:680–685 (1970)] without reducing the sample with dithiothreitol. The molecular weight is determined relative to prestained molecular weight standards (Bethesda Research Labs). Following autoradiography of the unfixed gel the approximate 28,000–30,000 dalton band is excised and the protein electrophoretically eluted from the gel (Hunkapillar et al supra). Based on similar purified bone fractions as described in the co-pending "BMP" applications described above wherein bone and/or cartilage activity is found in the 28,000–30,000 region, it is inferred that this band comprises bone and/or cartilage inductive fractions.

B. Subunit Characterization

The subunit composition of the isolated bovine bone protein is also determined. The eluted protein described above is fully reduced and alkylated in 2% SDS using iodoacetate and standard procedures and reconcentrated by electrophoretic packing. The fully reduced and alkylated sample is then further submitted to SDS-PAGE on a 12% gel and the resulting approximate 14,000–20,000 dalton region having a doublet appearance located by autoradiography of the unfixed gel. A faint band remains at the 28,000–30,000 region. Thus the 28,000–30,000 dalton protein yields a broad region of 14,000–20,000 which may otherwise also be interpreted and described as comprising two broad bands of approximately 14,000–16,000 and 16,000–18,000 daltons.

EXAMPLE III

Rosen Modified Sampath-Reddi Assay

A modified version of the rat bone formation assay described in Sampath and Reddi, *Proc. Natl. Acad. Sci. U.S.A.*, 80:6591–6595 (1983) is used to evaluate bone and/or cartilage activity of the proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [See, A. H. Reddi et al., *Proc. Natl Acad Sci.*, 69:1601 (1972)].

The other half of each implant is fixed and processed for histological analysis. Glycolmethacrylate sections (1 µm) are stained with Von Kossa and acid fuschin or toluidine blue to score the amount of induced bone and cartilage formation present in each implant. The terms +1 through +5 represent the area of each histological section of an implant occupied by new bone and/or cartilage cells and newly formed bone matrix. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone.

It is contemplated that the dose response nature of the cartilage and/or bone inductive protein containing samples of the matrix samples will demonstrate that the amount of bone and/or cartilage formed increases with the amount of cartilage/bone inductive protein in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI. To estimate the purity of the protein in a particular fraction an extinction coefficient of 1 OD/mg-cm is used as an estimate for protein and the protein is run on SDS PAGE followed by silver staining or radioiodination and autoradiography.

EXAMPLE IV

Bovine Protein Composition

The gel slice of the approximate 14,000–20,000 dalton region described in Example IIB is fixed with methanol-acetic acid-water using standard procedures, briefly rinsed with water, then neutralized with 0.1M ammonium bicarbonate. Following dicing the gel slice with a razor blade, the protein is digested from the gel matrix by adding 0.2 μg of TPCK-treated trypsin (Worthington) and incubating the gel for 16 hr. at 37 degrees centigrade. The resultant digest is then subjected to RPHPLC using a C4 Vydac RPHPLC column and 0.1% TFA-water 0.1% TFA water-acetonitrile gradient. The resultant peptide peaks were monitored by UV absorbance at 214 and 280 nm and subjected to direct amino terminal amino acid sequence analysis using an Applied Biosystems gas phase sequenator (Model 470A). One tryptic fragment is isolated by standard procedures having the following amino acid sequence as represented by the amino acid standard three-letter symbols and where "Xaa" indicates an unknown amino acid the amino acid in parentheses indicates uncertainty in the sequence:

Xaa-His-Glu-Leu-Tyr-Val-Ser-Phe-(Ser)

The following four oligonucleotide probes are designed on the basis of the amino acid sequence of the above-identified tryptic fragment and synthesized on an automated DNA synthesizer.
PROBE #1: GTRCTYGANATRCANTC
PROBE #2: GTRCTYGANATRCANAG
PROBE #3: GTRCTYAAYATRCANTC
PROBE #4: GTRCTYAAYATRCANAG The standard nucleotide symbols in the above identified probes are as follows: A,adenosine; C,cytosine; G,guanine; T,thymine; N, adenosine or cytosine or guanine or thymine; R,adenosine or guanine; and Y,-cytosine or thymine.

Each of the probes consists of pools of oligonucleotides. Because the genetic code is degenerate (more than one codon can code for the same amino acid), a mixture of oligonucleotides is synthesized that contains all possible nucleotide sequences encoding the amino acid sequence of the tryptic. These probes are radioactively labeled and employed to screen a bovine cDNA library as described below.

Poly(A) containing RNA is isolated by oligo(dT) cellulose chromatography from total RNA isolated from fetal bovine bone cells by the method of Gehron-Robey et al in *Current Advances in SkeletogenesiS*, Elsevier Science Publishers (1985). The total RNA was obtained from Dr. Marion Young, National Institute of Dental Research, National Institutes of Health. A cDNA library is made in lambda gt10 (Toole et al supra) and plated on 50 plates at 8000 recombinants per plate. These recombinants (400,000) are screened on duplicate nitrocellulose filters with a combination of Probes 1, 2, 3, and 4 using the Tetramethylammonium chloride (TMAC) hybridization procedure [see Wozney et al *Science*, 242: 1528–1534 (1988)]. Twenty-eight positives are obtained and are replated for secondaries. Duplicate nitrocellulose replicas again are made. One set of filters are screened with Probes 1 and 2; the other with Probes 3 and 4. Six positives are obtained on the former, 21 positives with the latter. One of the six, called HEL5, is plague purified, a phage plate stock made, and bacteriophage DNA isolated. This DNA is digested with EcoRI and subcloned into M13 and pSP65. The DNA sequence and derived amino acid sequence of this fragment is shown in FIG. 1 (SEQ ID NO: 1 and 2).

DNA sequence analysis of this fragment in M13 indicates that it encodes the desired tryptic peptide sequence set forth above, and this derived amino acid sequence is preceded by a basic residue (Lys) as predicted by the specificity of trypsin. The underlined portion of the sequence in FIG. 1 from amino acid #42 to #48 corresponds to the tryptic fragment identified above from which the oligonucleotide probes are designed. The derived amino acid sequence Ser-Gly-Ser-His-Gln-Asp-Ser-Ser-Arg as set forth in FIG. 1 from amino acid #15 to #23 is noted to be similar to a tryptic fragment sequence Ser-Thr-Pro-Ala-Gln-Asp-Val-Ser-Arg found in the 28,000–30,000 dalton purified bone preparation as described in the "BMP" co-pending application Ser. Nos. 179,101, 179,100, and 179,197 mentioned above. This fragment set forth in FIG. 1 is a portion of the DNA sequence which encodes a bovine BMP-5 protein further described in copending U.S. patent application Ser. No. 329,610. The DNA sequence indicates an open reading frame from the 5' end of the clone of 420 base pairs, encoding a partial peptide of 140 amino acid residues (the first 7 nucleotides are of the adaptors used in the cloning procedure). An in-frame stop codon (TAA) indicates that this clone encodes the carboxy-terminal part of bovine BMP-5.

The remaining positive clones isolated with probes #1, #2, #3, and #4 described above are screened with HEL5 and a further clone is identified that hybridizes under reduced hybridization conditions [5x SSC, 0.1% SDS, 5X Denhardt's, 100 μg/ml salmon sperm DNA standard hybridization buffer (SHB) at 65° C., wash in 2X SSC 0.1% SDS at 65° C.]. This clone is plaque purified, a phage plate stock made and bacteriophage DNA isolated. The DNA sequence and derived amino acid sequence of a portion of this clone is shown in FIG. 2 (SEQ ID NO: 3 and 4). This sequence represents the DNA sequence encoding a BMP-6 cartilage/bone protein of the invention.

The first underlined portion of the sequence in FIG. 2 from amino acid #97–amino acid #105 corresponds to the tryptic fragment found in the 28,000–30,000 dalton purified bovine bone preparation (and its reduced form at approximately 18,000–20,000 dalton reduced form) as described in the "BMP" co-pending applications mentioned above. The second underlined sequence in FIG. 2 from amino acid #124–amino acid #130 corresponds to the tryptic fragment identified above from which the oligonucleotide probes are designed.

The DNA sequence of FIG. 2 indicates an open reading frame of 666 base pairs starting from the 5'end of the sequence of FIG. 2, encoding a partial peptide of 222 amino acid residues. An in-frame stop codon (TGA) indicates that this clone encodes the carboxy-terminal part of a bovine BMP-6 protein of the invention. Based on knowledge of other BMP proteins and other proteins in the TGF-β family, it is predicted that the precursor polypeptide would be cleaved at the three basic residues (ArgArgArg) to yield a mature peptide beginning with residue 90 or 91 of the sequence of FIG. 2.

When the tryptic sequence His-Glu-Leu-Tyr-Val-Ser-Phe-(Ser) described above was identified, it was noted to be similar to the sequence His-Pro-Leu-Tyr-Val-Asp-Phe-Ser found in the bovine and human cartilage/bone protein BMP-2A sequence described in co-pending U.S. application Ser. No. 179,100. The amino acid sequences of the BMP-5 and BMP-6 polypeptides as set forth in FIGS. 1 and 2 (SEQ ID NO: 8 and 10) show significant homology to each other, as well as to BMP-2A; the DNA sequences encoding these proteins are also homologous. The carboxy-terminal 102 amino acid residues of bovine BMP-5 and BMP-6 have 89% identity. The DNA sequences of bovine BMP-5 and BMP-6 have approximately 78% sequence similarity. Furthermore, the carboxy-terminal 102 amino acid residues of bovine BMP-5 has 59% sequence identity with the carboxy-terminal 101 amino acid residues of human BMP-2A; BMP-6 and BMP-2A have 61% sequence identity over similar regions. The DNA sequences of bovine BMP-5 and human BMP-2A are approximately 64% similar; those of bovine BMP-6 and human BMP-2A are 66% similar.

EXAMPLE V

Human Proteins

Human cell lines which synthesize BMP-5 and/or BMP-6 mRNAs are identified in the following manner. RNA is isolated from a variety of human cell lines, selected for poly(A)-containing RNA by chromatography on oligo(dT) cellulose, electrophoresed on a formaldehyde-agarose gel, and transferred to nitrocellulose. A nitrocellulose replica of the gel is hybridized to a single standed M13 $^{32}$P-labeled probe corresponding to the above mentioned BMP-5 EcoRI-BglII fragment containing nucleotides 1–465 of the sequence of FIG. 1. A strongly hybridizing band is detected in the lane corresponding to the human osteosarcoma cell line U-2OS RNA. Another nitrocellulose replica is hybridized to a single stranded M13 $^{32}$P-labeled probe containing the PstI-SmaI fragment of bovine BMP-6 (corresponding to nucleotides 106–261 of FIG. 2). It is found that several RNA species in the lane corresponding to U-2OS RNA hybridize to this probe.

A cDNA Library is made in the vector lambda ZAP (Stratagene) from U-2OS poly(A)-containing RNA using established techniques (Toole et al.). 750,000 recombinants of this library are plated and duplicate nitrocellulose replicas made. The SmaI fragment of bovine BMP-6 corresponding to nucleotides 259–751 of FIG. 2 is labeled by nick-translation and hybridized to both sets of filters in SHB at 65°. One set of filters is washed under stringent conditions (0.2X SSC, 0.1% SDS at 65°), the other under reduced stringency conditions (1X SSC, 0.1% SDS at 65°). Many duplicate hybridizing recombinants (approximately 162) are noted. 24 are picked and replated for secondaries. Three nitrocellulose replicas are made of each plate. One is hybridized to the BMP-6 SmaI probe, one to a nick-translated BMP-6 PstI-SacI fragment (nucleotides 106–378 of FIG. 2), and the third to the nick-translated BMP-5 XbaI fragments (nucleotides 1–76 of FIG. 1). Hybridization and washes are carried out under stringent conditions.

Six clones which hybridize to the second probe more strongly than to the third are picked and transformed into plasmids. Restriction mapping, Southern blot analysis, and DNA sequence analysis of these plasmids indicate that there are two classes of clones. Clones U2-7and U2-10 contain human BMP-6 coding sequence based on their stronger hybridization to the second probe and closer DNA homology to the bovine BMP-6 sequence of FIG. 2 than the other 4 clones. DNA sequence derived from these clones is given in FIG. 3 (SEQ ID NO: 5). This sequence encodes a partial polypeptide of 132 amino acids comprising the carboxy-terminus of the human BMP-6 protein. A stop codon (TAA) follows the 396 base pairs of coding sequence. U2-7 was deposited with the American Type Culture Collection (ATCC), Rockville, Md. on Jun. 22, 1989 under accession number ATCC 68021.

The other four clones encode a novel polypeptide which we designate as BMP-7. Preliminary sequence data of a portion of clone U2-5 is given in FIG. 4 and encodes a partial polypeptide of 104 amino acid residues including the carboxy-terminus of the protein based on the presence of a stop codon (TAG) following an open reading frame of 312 bases. The derived amino acid sequence is very homologous to the human and bovine BMP-5 and BMP-6 sequences, and in addition shares homology with BMP-2 and BMP-4. U2-5 was deposited with the ATCC on Jun. 22, 1989 under accession number ATCC 68020.

Final sequence data of U2-5 reveals a cDNA sequence of 1259 nucleotides shown in FIG. 5 (SEQ ID NO: 9) encoding a polypeptide of 400 amino acids (SEQ ID NO: 10). Based on knowledge of other BMP proteins as well as other proteins within the TGF-β family, BMP-7 DNA is expected to encode a primary translation product which is processed to yield BMP-7 protein.

The corresponding bovine and human BMP-7 genes can be isolated using as probes the cDNA sequence set forth in FIGS. 4 and 5.

Additional methods known to those skilled in the art may be used to isolate the genetic material encoding human and other species' cartilage/bone proteins of the invention.

EXAMPLE VI

Expression of the BMP-7 Proteins

In order to produce bovine, human or other mammalian proteins of the invention, the DNA encoding it is transferred into an appropriate expression vector and introduced into mammalian cells or other preferred eukaryotic or prokaryotic hosts by conventional genetic engineering techniques. It is contemplated that the preferred expression system for biologically active recombinant human proteins of the invention will be stably transformed mammalian cells. It is further contemplated that the preferred mammalian cells will be CHO cells. The transformed host cell is cultured and the BMP-7 proteins expressed thereby are recovered and purified. The recombinantly expressed BMP-7 proteins are free of proteinaceous materials with which they ordinarily are associated in nature.

In order to express of biologically active human BMP-7 a selected host cell is transformed, using techniques known to those skilled in the art of genetic engineering, with a DNA sequence encoding human BMP-7 protein. Such a DNA sequence comprises the DNA sequence from nucleotide #1 to #312 set forth in FIG. 4 or nucleotide #1 to #1200 of FIG. 5. The transformed host cells are cultured and the BMP-7 protein comprising the amino acid sequence from amino acid #1 to amino acid #104 as set forth in FIG. 4 or the amino acid sequence comprising #37 to #140 of FIG. 5 is expressed. The expressed protein is recovered, isolated and purified form the culture and culture medium. The purified protein is substantally free from other proteinaceous materials with which it is co-produced.

One skilled in the art can construct mammalian expression vectors by employing the DNA sequences of the invention sequences and known vectors, such as pCD [Okayama et al., Mol. Cell Biol., 2:161–170 (1982)] and pJL3, pJL4 [Gough et al., EMBO J., 4:645–653 (1985)]. The transformation of these vectors into appropriate host cells may result in expression of the proteins of the invention. One skilled in the art could manipulate the sequences of the invention by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences there-from or altering nucleotides therein by other known techniques). The modified coding sequence could then be inserted into a known bacterial vector using procedures such as described in T. Taniguchi et al., Proc. Natl Acad. Sci. USA, 77:5230–5233 (1980). This exemplary bacterial vector could then be transformed into bacterial host cells and a protein of the invention expressed thereby. For a strategy for producing extracellular expression of a cartilage and/or bone protein of the invention in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a protein of the invention from mammalian cells involves the construction of cells containing multiple copies of the heterologous gene encoding proteins of the invention. The heterologous gene may be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, J. Mol. Biol., 159:601–629 (1982). This approach can be employed with a number of different cell types. For example, a plasmid containing a DNA sequence for a protein of the invention in operative association with other plasmid sequences enabling expression thereof and the DHFR expression plasmid pAdA26SV(A)3 [Kaufman and Sharp, Mol. cell. Biol., 2:1304 (1982)] may be co-introduced into DHFR-deficient CHO cells, DUKX-BII, by calcium phosphate coprecipitation and transfection, electroperation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5 uM MTX) as described in Kaufman et al., Mol Cell Biol., 5:1750 (1983). Protein expression should increase with increasing levels of MTX resistance. Transformants are cloned, and the proteins of the invention are recovered, isolated, and purified from the culture medium. Biologically active protein expression is monitored by the Rosen-modified Sampath-Reddi rat bone formation assay described above in Example III. Similar procedures can be followed to produce other related proteins.

EXAMPLE VII

Biological Activity of Expressed BMP-7 Proteins

To measure the biological activity of the expressed proteins obtained in Example VI above the BMP-7 proteins are recovered from the culture media and purified. BMP-7 may be partially purified on a Heparin Sepharose column. 4 ml of the collected post transfection conditioned medium supernatant from one 100 mm culture dish is concentrated approximately 10 fold by ultrafiltration on a YM 10 membrane and then dialyzed against 20 mM Tris, 0.15M NaCl, pH 7.4 (starting buffer). This material is then applied to a 1.1 ml Heparin Sepharose column in starting buffer. Unbound proteins are removed by an 8 ml wash of starting buffer, and bound proteins, including proteins of the invention, are desorbed by a 3–4 ml wash of 20 mM Tris, 2.0M NaCl, pH 7.4.

The proteins bound by the Heparin column are concentrated approximately 10-fold on a Centricon 10 and the salt reduced by diafiltration with 0.1% trifluoroacetic acid. The appropriate amount of this solution is mixed with 20 mg of rat matrix and then assayed for in vivo bone and/or cartilage formation activity by the Rosen-modified Sampath-Reddi assay. A mock transfection supernatant fractionation is used as a control.

The implants containing rat matrix to which specific amounts of human proteins of the invention have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Levels of activity may also be tested for host cell extracts. Partial purification is accomplished in a similar manner as described above except that 6M urea is included in all the buffers.

The procedures described above may be employed to isolate other related proteins of interest by utilizing the bovine or human proteins as a probe source. Such other proteins may find similar utility in, inter alia, fracture repair, wound healing and tissue repair.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A method for producing a BMP-7 protein which comprises transforming mammalian cells with an expression vector, said vector having inserted therein a DNA sequence which encodes the amino acid sequence of SEQ ID NO: 8, culturing said cells in a suitable culture medium, and isolating said BMP-7 protein produced by said cells.

2. A method for producing a BMP-7 protein which comprises transforming mammalian cells with an expression vector, said vector having inserted therein a DNA sequence comprising the DNA sequence of SEQ ID NO: 7 which encodes the amino acid sequence of SEQ ID NO: 8, culturing said cells in a suitable culture medium, and isolating said BMP-7 protein produced by said cells.

3. A method for producing a BMP-7 protein which comprises transforming mammalian cells with an expression vector, said vector having inserted therein a DNA sequence comprising the DNA sequence of SEQ ID NO: 7 and sequences which
   a) hybridize to the sequence of SEQ ID NO: 7 under stringent hybridization conditions; and
   b) express a protein characterized by the ability to induce the formation of cartilage and/or bone formation in the Rosen-modified Sampath Reddi assay
culturing said cells in a suitable culture medium, and isolating said BMP-7 protein produced by said cells.

4. The method of claims 1, 2, or 3 wherein said mammalian cells are CHO cells.

5. A method for producing a BMP-7 protein which comprises transforming mammalian cells with an expression vector, said vector having inserted therein a DNA sequence which encodes the amino acid sequence of SEQ ID NO: 10, culturing said cells in a suitable culture medium, and isolating said BMP-7 protein produced by said cells.

6. A method for producing a BMP-7 protein which comprises transforming mammalian cells with an expression vector, said vector having inserted therein a DNA sequence comprising the DNA sequence of SEQ ID NO: 9 which encodes the amino acid sequence of SEQ ID NO: 10, culturing said cells in a suitable culture medium, and isolating said BMP-7 protein produced by said cells.

7. A method for producing a BMP-7 protein which comprises transforming mammalian cells with an expression vector, said vector having inserted therein a DNA sequence comprising the DNA sequence of SEQ ID NO: 9 and sequences which
   a) hybridize to the sequence of SEQ ID NO: 9 under stringent hybridization conditions; and
   b) express a protein characterized by the ability to induce the formation of catilage and/or bone in the Rosen-modified Sampath Reddi assay
culturing said cells in a suitable culture medium, and isolating said BMP-7 protein produced by said cells.

8. The method of claims 5, 6, or 7 wherein said mammalian cells are CHO cells.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 578 base pairs
        ( B ) TYPE: nucleic acid
        ( C ) STRANDEDNESS: double
        ( D ) TOPOLOGY: circular ( i i ) MOLECULE TYPE: cDNA to mRNA ( i i i ) HYPOTHETICAL: NO ( i v ) ANTI-SENSE: NO ( v ) FRAGMENT TYPE: C-terminal ( v i ) ORIGINAL SOURCE:
        ( A ) ORGANISM: Bos taurus
        ( F ) TISSUE TYPE: Fetal long bone ( v i i ) IMMEDIATE SOURCE:
        ( A ) LIBRARY: bovine bone cDNA library
        ( B ) CLONE: HEL5

( v i i i ) POSITION IN GENOME:
        ( C ) UNITS: bp ( i x ) FEATURE:
        ( A ) NAME/KEY: CDS
        ( B ) LOCATION: 8..427

( i x ) FEATURE:
        ( A ) NAME/KEY: matpeptide
        ( B ) LOCATION: 13..427

( i x ) FEATURE:
        ( A ) NAME/KEY: mRNA
        ( B ) LOCATION: 7..578

( x i ) SEQUENCE DESCRIPTION: SEQ ID NO:1:

```
TCTAGAG GTG AGA GCA GCC AAC AAG AGA AAA AAT CAA AAC CGC AAT AAA            49
        Val Arg Ala Ala Asn Lys Arg Lys Asn Gln Asn Arg Asn Lys
         -1   1           5                  10

TCC GGC TCT CAT CAG GAC TCC TCT AGA ATG TCC AGT GTT GGA GAT TAT            97
Ser Gly Ser His Gln Asp Ser Ser Arg Met Ser Ser Val Gly Asp Tyr
         15              20              25

AAC ACC AGT GAA CAA AAA CAA GCC TGT AAA AAG CAT GAA CTC TAT GTG           145
Asn Thr Ser Glu Gln Lys Gln Ala Cys Lys Lys His Glu Leu Tyr Val
30              35              40                          45

AGT TTC CGG GAT CTG GGA TGG CAG GAC TGG ATT ATA GCA CCA GAA GGA           193
Ser Phe Arg Asp Leu Gly Trp Gln Asp Trp Ile Ile Ala Pro Glu Gly
                 50              55                      60

TAT GCT GCA TTT TAT TGT GAT GGA GAA TGT TCT TTT CCA CTC AAT GCC           241
Tyr Ala Ala Phe Tyr Cys Asp Gly Glu Cys Ser Phe Pro Leu Asn Ala
             65              70                  75

CAT ATG AAT GCC ACC AAT CAT GCC ATA GTT CAG ACT CTG GTT CAC CTG           289
His Met Asn Ala Thr Asn His Ala Ile Val Gln Thr Leu Val His Leu
         80              85                  90

ATG TTT CCT GAC CAC GTA CCA AAG CCT TGC TGC GCG ACA AAC AAA CTA           337
Met Phe Pro Asp His Val Pro Lys Pro Cys Cys Ala Thr Asn Lys Leu
     95              100                 105

AAT GCC ATC TCT GTG TTG TAC TTT GAT GAC AGC TCC AAT GTC ATT TTG           385
Asn Ala Ile Ser Val Leu Tyr Phe Asp Asp Ser Ser Asn Val Ile Leu
110             115                 120                 125
```

| AAA AAG TAC AGA AAT ATG GTC GTG CGT TCG TGT GGT TGC CAC | 427 |
| Lys Lys Tyr Arg Asn Met Val Val Arg Ser Cys Gly Cys His | |
| 130 135 | |

| TAATAGTGCA TAATAATGGT AATAAGAAAA AAGATCTGTA TGGAGGTTTA TGACTACAAT | 487 |

| AAAAAATATC TTTCGGATAA AAGGGGAATT TAATAAAATT AGTCTGGCTC ATTTCATCTC | 547 |

| TGTAACCTAT GTACAAGAGC ATGTATATAG T | 578 |

( 2 ) INFORMATION FOR SEQ ID NO:2:

( i ) SEQUENCE CHARACTERISTICS:
        ( A ) LENGTH: 140 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Val Arg Ala Ala Asn Lys Arg Lys Asn Gln Asn Arg Asn Lys Ser Gly
 -1   1               5                  10                  15

Ser His Gln Asp Ser Ser Arg Met Ser Ser Val Gly Asp Tyr Asn Thr
             20                  25                  30

Ser Glu Gln Lys Gln Ala Cys Lys Lys His Glu Leu Tyr Val Ser Phe
             35                  40                  45

Arg Asp Leu Gly Trp Gln Asp Trp Ile Ile Ala Pro Glu Gly Tyr Ala
         50                  55                  60

Ala Phe Tyr Cys Asp Gly Glu Cys Ser Phe Pro Leu Asn Ala His Met
     65                  70                  75

Asn Ala Thr Asn His Ala Ile Val Gln Thr Leu Val His Leu Met Phe
 80                  85                  90                  95

Pro Asp His Val Pro Lys Pro Cys Cys Ala Thr Asn Lys Leu Asn Ala
                 100                 105                 110

Ile Ser Val Leu Tyr Phe Asp Asp Ser Ser Asn Val Ile Leu Lys Lys
             115                 120                 125

Tyr Arg Asn Met Val Val Arg Ser Cys Gly Cys His
             130                 135
```

( 2 ) INFORMATION FOR SEQ ID NO:3:

( i ) SEQUENCE CHARACTERISTICS:
        ( A ) LENGTH: 894 base pairs
        ( B ) TYPE: nucleic acid
        ( C ) STRANDEDNESS: double
        ( D ) TOPOLOGY: circular ( i i ) MOLECULE TYPE: cDNA to mRNA ( i i i ) HYPOTHETICAL: NO ( v ) FRAGMENT TYPE: C-terminal ( v i ) ORIGINAL SOURCE:
        ( A ) ORGANISM: Bos taurus
        ( F ) TISSUE TYPE: Fetal long bone ( v i i ) IMMEDIATE SOURCE:
        ( A ) LIBRARY: Bovine bone cDNA library
        ( B ) CLONE: HEL16

( v i i i ) POSITION IN GENOME:
        ( C ) UNITS: bp ( i x ) FEATURE:
        ( A ) NAME/KEY: CDS
        ( B ) LOCATION: 1..669

( i x ) FEATURE:
        ( A ) NAME/KEY: matpeptide
        ( B ) LOCATION: 250..666

(ix) FEATURE:
  (A) NAME/KEY: mRNA
  (B) LOCATION: 1..894

(xi) SEQUENCE DESCRIPTION: SEQ ID NO:3:

```
CTG CTG GGC ACG CGT GCT GTG TGG GCC TCA GAG GCG GGC TGG CTG GAG         48
Leu Leu Gly Thr Arg Ala Val Trp Ala Ser Glu Ala Gly Trp Leu Glu
-83         -80              -75              -70

TTT GAC ATC ACG GCC ACC AGC AAC CTG TGG GTC CTG ACT CCG CAG CAC         96
Phe Asp Ile Thr Ala Thr Ser Asn Leu Trp Val Leu Thr Pro Gln His
        -65              -60              -55

AAC ATG GGG CTG CAG CTG AGC GTG GTC ACG CGT GAT GGG CTC AGC ATC        144
Asn Met Gly Leu Gln Leu Ser Val Val Thr Arg Asp Gly Leu Ser Ile
    -50              -45              -40

AGC CCT GGG GCC GCG GGC CTG GTG GGC AGG GAC GGC CCC TAC GAC AAG        192
Ser Pro Gly Ala Ala Gly Leu Val Gly Arg Asp Gly Pro Tyr Asp Lys
-35              -30              -25              -20

CAG CCC TTC ATG GTG GCC TTC TTC AAG GCC AGT GAG GTC CAC GTG CGC        240
Gln Pro Phe Met Val Ala Phe Phe Lys Ala Ser Glu Val His Val Arg
            -15              -10                  -5

AGT GCC CGG TCG GCC CCC GGG CGG CGC CGG CAG CAG GCC CGG AAC CGC        288
Ser Ala Arg Ser Ala Pro Gly Arg Arg Arg Gln Gln Ala Arg Asn Arg
            1               5                   10

TCC ACC CCG GCC CAG GAC GTG TCG CGG GCC TCC AGC GCC TCA GAC TAC        336
Ser Thr Pro Ala Gln Asp Val Ser Arg Ala Ser Ser Ala Ser Asp Tyr
    15              20                  25

AAC AGC AGC GAG CTG AAG ACG GCC TGC CGG AAG CAT GAG CTC TAC GTG        384
Asn Ser Ser Glu Leu Lys Thr Ala Cys Arg Lys His Glu Leu Tyr Val
30                  35              40                      45

AGC TTC CAG GAC CTG GGG TGG CAG GAC TGG ATC ATT GCC CCC AAG GGC        432
Ser Phe Gln Asp Leu Gly Trp Gln Asp Trp Ile Ile Ala Pro Lys Gly
                50                  55                  60

TAC GCT GCC AAC TAC TGT GAC GGA GAA TGT TCG TTC CCT CTC AAC GCA        480
Tyr Ala Ala Asn Tyr Cys Asp Gly Glu Cys Ser Phe Pro Leu Asn Ala
            65                  70                  75

CAC ATG AAC GCT ACC AAC CAT GCC ATC GTG CAG ACC CTG GTT CAC CTC        528
His Met Asn Ala Thr Asn His Ala Ile Val Gln Thr Leu Val His Leu
        80                  85                  90

ATG AAC CCC GAG TAC GTC CCC AAA CCG TGC TGC GCG CCC ACG AAA CTG        576
Met Asn Pro Glu Tyr Val Pro Lys Pro Cys Cys Ala Pro Thr Lys Leu
    95                  100                 105

AAC GCC ATC TCG GTG CTC TAC TTC GAC GAC AAC TCC AAT GTC ATC CTG        624
Asn Ala Ile Ser Val Leu Tyr Phe Asp Asp Asn Ser Asn Val Ile Leu
110                 115                 120                 125

AAG AAG TAC CGG AAC ATG GTC GTA CGA GCG TGT GGG TGC CAC TGACTCGGGG    676
Lys Lys Tyr Arg Asn Met Val Val Arg Ala Cys Gly Cys His
                130                 135                 140

TGAGTGGCTG GGGACGCTGT GCACACACTG CCTGGACTCC TGGATCACGT CCGCCTTAAG     736

CCCACAGAGG CCCCCGGGAC ACAGGAGGAG ACCCCGAGGC CACCTTCGGC TGGCGTTGGC     796

CTTTCCGCCC AACGCAGACC CGAAGGGACC CTGTCCGCCC CTTGCTCACA CCGTGAGCGT     856

TGTGAGTAGC CATCGGGCTC TAGGAAGCAG CACTCGAG                             894
```

(2) INFORMATION FOR SEQ ID NO:4:

(i) SEQUENCE CHARACTERISTICS:
    (A) LENGTH: 222 amino acids
    (B) TYPE: amino acid
    (D) TOPOLOGY: linear (ii) MOLECULE TYPE: protein (xi) SEQUENCE DESCRIPTION: SEQ ID NO:4:

| Leu | Leu | Gly | Thr | Arg | Ala | Val | Trp | Ala | Ser | Glu | Ala | Gly | Trp | Leu | Glu |
| -83 |     | -80 |     |     |     |     | -75 |     |     |     |     | -70 |     |     |     |

| Phe | Asp | Ile | Thr | Ala | Thr | Ser | Asn | Leu | Trp | Val | Leu | Thr | Pro | Gln | His |
|     |     | -65 |     |     |     |     | -60 |     |     |     |     | -55 |     |     |     |

| Asn | Met | Gly | Leu | Gln | Leu | Ser | Val | Val | Thr | Arg | Asp | Gly | Leu | Ser | Ile |
|     | -50 |     |     |     |     | -45 |     |     |     |     | -40 |     |     |     |     |

| Ser | Pro | Gly | Ala | Ala | Gly | Leu | Val | Gly | Arg | Asp | Gly | Pro | Tyr | Asp | Lys |
| -35 |     |     |     |     | -30 |     |     |     |     | -25 |     |     |     |     | -20 |

| Gln | Pro | Phe | Met | Val | Ala | Phe | Phe | Lys | Ala | Ser | Glu | Val | His | Val | Arg |
|     |     |     |     | -15 |     |     |     |     | -10 |     |     |     |     | -5  |     |

| Ser | Ala | Arg | Ser | Ala | Pro | Gly | Arg | Arg | Arg | Gln | Gln | Ala | Arg | Asn | Arg |
|     |     |     | 1   |     |     |     | 5   |     |     |     |     | 10  |     |     |     |

| Ser | Thr | Pro | Ala | Gln | Asp | Val | Ser | Arg | Ala | Ser | Ser | Ala | Ser | Asp | Tyr |
|     | 15  |     |     |     |     | 20  |     |     |     |     | 25  |     |     |     |     |

| Asn | Ser | Ser | Glu | Leu | Lys | Thr | Ala | Cys | Arg | Lys | His | Glu | Leu | Tyr | Val |
| 30  |     |     |     |     | 35  |     |     |     |     | 40  |     |     |     |     | 45  |

| Ser | Phe | Gln | Asp | Leu | Gly | Trp | Gln | Asp | Trp | Ile | Ile | Ala | Pro | Lys | Gly |
|     |     |     |     | 50  |     |     |     |     | 55  |     |     |     |     | 60  |     |

| Tyr | Ala | Ala | Asn | Tyr | Cys | Asp | Gly | Glu | Cys | Ser | Phe | Pro | Leu | Asn | Ala |
|     |     |     | 65  |     |     |     |     | 70  |     |     |     |     | 75  |     |     |

| His | Met | Asn | Ala | Thr | Asn | His | Ala | Ile | Val | Gln | Thr | Leu | Val | His | Leu |
|     |     | 80  |     |     |     |     | 85  |     |     |     |     | 90  |     |     |     |

| Met | Asn | Pro | Glu | Tyr | Val | Pro | Lys | Pro | Cys | Cys | Ala | Pro | Thr | Lys | Leu |
|     | 95  |     |     |     |     | 100 |     |     |     |     | 105 |     |     |     |     |

| Asn | Ala | Ile | Ser | Val | Leu | Tyr | Phe | Asp | Asp | Asn | Ser | Asn | Val | Ile | Leu |
| 110 |     |     |     |     | 115 |     |     |     |     | 120 |     |     |     |     | 125 |

| Lys | Lys | Tyr | Arg | Asn | Met | Val | Val | Arg | Ala | Cys | Gly | Cys | His |
|     |     |     |     | 130 |     |     |     |     | 135 |     |     |     |     |

( 2 ) INFORMATION FOR SEQ ID NO:5:

( i ) SEQUENCE CHARACTERISTICS:
        ( A ) LENGTH: 400 base pairs
        ( B ) TYPE: nucleic acid
        ( C ) STRANDEDNESS: double
        ( D ) TOPOLOGY: circular ( i i ) MOLECULE TYPE: cDNA to mRNA ( i i i ) HYPOTHETICAL: NO ( v ) FRAGMENT TYPE: C-terminal ( v i ) ORIGINAL SOURCE:
        ( A ) ORGANISM: Homo sapiens
        ( H ) CELL LINE: U2-OS Osteosarcoma ( v i i ) IMMEDIATE SOURCE:
        ( A ) LIBRARY: U2-OS human osteosarcoma cDNA library
        ( B ) CLONE: U2-7

( v i i i ) POSITION IN GENOME:
        ( C ) UNITS: bp ( i x ) FEATURE:
        ( A ) NAME/KEY: CDS
        ( B ) LOCATION: 1..399

( i x ) FEATURE:
        ( A ) NAME/KEY: matpeptide
        ( B ) LOCATION: 1..400

( i x ) FEATURE:
        ( A ) NAME/KEY: mRNA
        ( B ) LOCATION: 1..400

( x i ) SEQUENCE DESCRIPTION: SEQ ID NO:5:

-continued

| | | | | | | | | | | | | | | | | |
|---|---|---|---|---|---|---|---|---|---|---|---|---|---|---|---|---|
| CAA | CAG | AGT | CGT | AAT | CGC | TCT | ACC | CAG | TCC | CAG | GAC | GTG | GCG | CGG | GTC | 48 |
| Gln | Gln | Ser | Arg | Asn | Arg | Ser | Thr | Gln | Ser | Gln | Asp | Val | Ala | Arg | Val | |
| 1 | | | | 5 | | | | | 10 | | | | | 15 | | |
| TCC | AGT | GCT | TCA | GAT | TAC | AAC | AGC | AGT | GAA | TTG | AAA | ACA | GCC | TGC | AGG | 96 |
| Ser | Ser | Ala | Ser | Asp | Tyr | Asn | Ser | Ser | Glu | Leu | Lys | Thr | Ala | Cys | Arg | |
| | | | 20 | | | | | 25 | | | | | 30 | | | |
| AAG | CAT | GAG | CTG | TAT | GTG | AGT | TTC | CAA | GAC | CTG | GGA | TGG | CAG | GAC | TGG | 144 |
| Lys | His | Glu | Leu | Tyr | Val | Ser | Phe | Gln | Asp | Leu | Gly | Trp | Gln | Asp | Trp | |
| | | 35 | | | | | 40 | | | | | 45 | | | | |
| ATC | ATT | GCA | CCC | AAG | GGC | TAT | GCT | GCC | AAT | TAC | TGT | GAT | GGA | GAA | TGC | 192 |
| Ile | Ile | Ala | Pro | Lys | Gly | Tyr | Ala | Ala | Asn | Tyr | Cys | Asp | Gly | Glu | Cys | |
| | | 50 | | | | 55 | | | | | 60 | | | | | |
| TCC | TTC | CCA | CTC | AAC | GCA | CAC | ATG | AAT | GCA | ACC | AAC | CAC | GCG | ATT | GTG | 240 |
| Ser | Phe | Pro | Leu | Asn | Ala | His | Met | Asn | Ala | Thr | Asn | His | Ala | Ile | Val | |
| 65 | | | | | 70 | | | | | 75 | | | | | 80 | |
| CAG | ACC | TTG | GTT | CAC | CTT | ATG | AAC | CCC | GAG | TAT | GTC | CCC | AAA | CCG | TGC | 288 |
| Gln | Thr | Leu | Val | His | Leu | Met | Asn | Pro | Glu | Tyr | Val | Pro | Lys | Pro | Cys | |
| | | | | 85 | | | | | 90 | | | | | 95 | | |
| TGT | GCG | CCA | ACT | AAG | CTA | AAT | GCC | ATC | TCG | GTT | CTT | TAC | TTT | GAT | GAC | 336 |
| Cys | Ala | Pro | Thr | Lys | Leu | Asn | Ala | Ile | Ser | Val | Leu | Tyr | Phe | Asp | Asp | |
| | | | 100 | | | | | 105 | | | | | 110 | | | |
| AAC | TCC | AAT | GTC | ATT | CTG | AAA | AAA | TAC | AGG | AAT | ATG | GTT | GTA | AGA | GCT | 384 |
| Asn | Ser | Asn | Val | Ile | Leu | Lys | Lys | Tyr | Arg | Asn | Met | Val | Val | Arg | Ala | |
| | | 115 | | | | | 120 | | | | | 125 | | | | |
| TGT | GGA | TGC | CAC | TAAC | | | | | | | | | | | | 400 |
| Cys | Gly | Cys | His | | | | | | | | | | | | | |
| | | 130 | | | | | | | | | | | | | | |

( 2 ) INFORMATION FOR SEQ ID NO:6:

( i ) SEQUENCE CHARACTERISTICS:
        ( A ) LENGTH: 132 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| | | | | | | | | | | | | | |
|---|---|---|---|---|---|---|---|---|---|---|---|---|---|
| Gln | Gln | Ser | Arg | Asn | Arg | Ser | Thr | Gln | Ser | Gln | Asp | Val | Ala | Arg | Val |
| 1 | | | | 5 | | | | | 10 | | | | | 15 | |
| Ser | Ser | Ala | Ser | Asp | Tyr | Asn | Ser | Ser | Glu | Leu | Lys | Thr | Ala | Cys | Arg |
| | | | 20 | | | | | 25 | | | | | 30 | | |
| Lys | His | Glu | Leu | Tyr | Val | Ser | Phe | Gln | Asp | Leu | Gly | Trp | Gln | Asp | Trp |
| | | 35 | | | | | 40 | | | | | 45 | | | |
| Ile | Ile | Ala | Pro | Lys | Gly | Tyr | Ala | Ala | Asn | Tyr | Cys | Asp | Gly | Glu | Cys |
| | | 50 | | | | 55 | | | | | 60 | | | | |
| Ser | Phe | Pro | Leu | Asn | Ala | His | Met | Asn | Ala | Thr | Asn | His | Ala | Ile | Val |
| 65 | | | | | 70 | | | | | 75 | | | | | 80 |
| Gln | Thr | Leu | Val | His | Leu | Met | Asn | Pro | Glu | Tyr | Val | Pro | Lys | Pro | Cys |
| | | | | 85 | | | | | 90 | | | | | 95 | |
| Cys | Ala | Pro | Thr | Lys | Leu | Asn | Ala | Ile | Ser | Val | Leu | Tyr | Phe | Asp | Asp |
| | | | 100 | | | | | 105 | | | | | 110 | | |
| Asn | Ser | Asn | Val | Ile | Leu | Lys | Lys | Tyr | Arg | Asn | Met | Val | Val | Arg | Ala |
| | | 115 | | | | | 120 | | | | | 125 | | | |
| Cys | Gly | Cys | His | | | | | | | | | | | | |
| | | 130 | | | | | | | | | | | | | |

( 2 ) INFORMATION FOR SEQ ID NO:7:

( i ) SEQUENCE CHARACTERISTICS:
        ( A ) LENGTH: 316 base pairs
        ( B ) TYPE: nucleic acid (C) STRANDEDNESS: double
(D) TOPOLOGY: circular (ii) MOLECULE TYPE: cDNA to mRNA (iii) HYPOTHETICAL: NO (v) FRAGMENT TYPE: C-terminal (vi) ORIGINAL SOURCE:
(A) ORGANISM: Homo sapiens
(H) CELL LINE: U2-OS osteosarcoma (vii) IMMEDIATE SOURCE:
(A) LIBRARY: U2-OS human osteosarcoma cDNA library
(B) CLONE: U2-5

(viii) POSITION IN GENOME:
(C) UNITS: bp (ix) FEATURE:
(A) NAME/KEY: CDS
(B) LOCATION: 1..315

(ix) FEATURE:
(A) NAME/KEY: matpeptide
(B) LOCATION: 1..312

(ix) FEATURE:
(A) NAME/KEY: mRNA
(B) LOCATION: 1..316

(xi) SEQUENCE DESCRIPTION: SEQ ID NO:7:

```
CAG GCC TGT AAG AAG CAC GAG CTG TAT GTC AGC TTC CGA GAC CTG GGC          48
Gln Ala Cys Lys Lys His Glu Leu Tyr Val Ser Phe Arg Asp Leu Gly
  1               5                  10                  15

TGG CAG GAC TGG ATC ATC GCG CCT GAA GGC TAC GCC GCC TAC TAC TGT          96
Trp Gln Asp Trp Ile Ile Ala Pro Glu Gly Tyr Ala Ala Tyr Tyr Cys
             20                  25                  30

GAG GGG GAG TGT GCC TTC CCT CTG AAC TCC TAC ATG AAC GCC ACC AAC         144
Glu Gly Glu Cys Ala Phe Pro Leu Asn Ser Tyr Met Asn Ala Thr Asn
         35                  40                  45

CAC GCC ATC GTG CAG ACG CTG GTC CAC TTC ATC AAC CCG GAA ACG GTG         192
His Ala Ile Val Gln Thr Leu Val His Phe Ile Asn Pro Glu Thr Val
     50                  55                  60

CCC AAG CCC TGC TGT GCG CCC ACG CAG CTC AAT GCC ATC TCC GTC CTC         240
Pro Lys Pro Cys Cys Ala Pro Thr Gln Leu Asn Ala Ile Ser Val Leu
 65                  70                  75                  80

TAC TTC GAT GAC AGC TCC AAC GTC ATC CTG AAG AAA TAC AGA AAC ATG         288
Tyr Phe Asp Asp Ser Ser Asn Val Ile Leu Lys Lys Tyr Arg Asn Met
                 85                  90                  95

GTG GTC CGG GCC TGT GGC TGC CAC TAGC                                    316
Val Val Arg Ala Cys Gly Cys His
                100                 105
```

(2) INFORMATION FOR SEQ ID NO:8:

(i) SEQUENCE CHARACTERISTICS:
(A) LENGTH: 104 amino acids
(B) TYPE: amino acid
(D) TOPOLOGY: linear (ii) MOLECULE TYPE: protein (xi) SEQUENCE DESCRIPTION: SEQ ID NO:8:

```
Gln Ala Cys Lys Lys His Glu Leu Tyr Val Ser Phe Arg Asp Leu Gly
  1               5                  10                  15

Trp Gln Asp Trp Ile Ile Ala Pro Glu Gly Tyr Ala Ala Tyr Tyr Cys
             20                  25                  30

Glu Gly Glu Cys Ala Phe Pro Leu Asn Ser Tyr Met Asn Ala Thr Asn
         35                  40                  45
```

```
His  Ala  Ile  Val  Gln  Thr  Leu  Val  His  Phe  Ile  Asn  Pro  Glu  Thr  Val
     50                  55                       60

Pro  Lys  Pro  Cys  Cys  Ala  Pro  Thr  Gln  Leu  Asn  Ala  Ile  Ser  Val  Leu
 65                 70                  75                                  80

Tyr  Phe  Asp  Asp  Ser  Ser  Asn  Val  Ile  Leu  Lys  Lys  Tyr  Arg  Asn  Met
                    85                  90                            95

Val  Val  Arg  Ala  Cys  Gly  Cys  His
               100
```

( 2 ) INFORMATION FOR SEQ ID NO:9:

( i ) SEQUENCE CHARACTERISTICS:
        ( A ) LENGTH: 1259 base pairs
        ( B ) TYPE: nucleic acid
        ( C ) STRANDEDNESS: double
        ( D ) TOPOLOGY: circular ( i i ) MOLECULE TYPE: cDNA to mRNA ( i i i ) HYPOTHETICAL: NO ( v ) FRAGMENT TYPE: C-terminal ( v i ) ORIGINAL SOURCE:
        ( A ) ORGANISM: Homo sapiens
        ( H ) CELL LINE: U2-OS Osteosarcoma ( v i i ) IMMEDIATE SOURCE:
        ( A ) LIBRARY: U2-OS Human Osteosarcoma cDNA library
        ( B ) CLONE: U2-5

( v i i i ) POSITION IN GENOME:
        ( C ) UNITS: bp ( i x ) FEATURE:
        ( A ) NAME/KEY: CDS
        ( B ) LOCATION: 1..1200

( i x ) FEATURE:
        ( A ) NAME/KEY: matpeptide
        ( B ) LOCATION: 783..1200

( i x ) FEATURE:
        ( A ) NAME/KEY: mRNA
        ( B ) LOCATION: 1..1259

( x i ) SEQUENCE DESCRIPTION: SEQ ID NO:9:

```
AGC  CTG  GAC  AAC  GAG  GTG  CAC  TCG  AGC  TTC  ATC  CAC  CGG  CGC  CTC  CGC         48
Ser  Leu  Asp  Asn  Glu  Val  His  Ser  Ser  Phe  Ile  His  Arg  Arg  Leu  Arg
-260                -255                     -250                          -245

AGC  CAG  GAG  CGG  CGG  GAG  ATG  CAG  CGC  GAG  ATC  CTC  TCC  ATT  TTG  GGC         96
Ser  Gln  Glu  Arg  Arg  Glu  Met  Gln  Arg  Glu  Ile  Leu  Ser  Ile  Leu  Gly
               -240                     -235                     -230

TTG  CCC  CAC  CGC  CCG  CGC  CCG  CAC  CTC  CAG  GGC  AAG  CAC  AAC  TCG  GCA        144
Leu  Pro  His  Arg  Pro  Arg  Pro  His  Leu  Gln  Gly  Lys  His  Asn  Ser  Ala
          -225                     -220                          -215

CCC  ATG  TTC  ATG  CTG  GAC  CTG  TAC  AAC  GCC  ATG  GCG  GTG  GAG  GAG  GGC        192
Pro  Met  Phe  Met  Leu  Asp  Leu  Tyr  Asn  Ala  Met  Ala  Val  Glu  Glu  Gly
     -210                          -205                     -200

GGC  GGG  CCC  GGC  GGC  CAG  GGC  TTC  TCC  TAC  CCC  TAC  AAG  GCC  GTC  TTC        240
Gly  Gly  Pro  Gly  Gly  Gln  Gly  Phe  Ser  Tyr  Pro  Tyr  Lys  Ala  Val  Phe
     -195                     -190                      -185

AGT  ACC  CAG  GGC  CCC  CCT  CTG  GCC  AGC  CTG  CAA  GAT  AGC  CAT  TTC  CTC        288
Ser  Thr  Gln  Gly  Pro  Pro  Leu  Ala  Ser  Leu  Gln  Asp  Ser  His  Phe  Leu
-180                -175                     -170                          -165

ACC  GAC  GCC  GAC  ATG  GTC  ATG  AGC  TTC  GTC  AAC  CTC  GTG  GAA  CAT  GAC        336
Thr  Asp  Ala  Asp  Met  Val  Met  Ser  Phe  Val  Asn  Leu  Val  Glu  His  Asp
                    -160                     -155                     -150

AAG  GAA  TTC  TTC  CAC  CCA  CGC  TAC  CAC  CAT  CGA  GAG  TTC  CGG  TTT  GAT        384
```

|     |     |     |     |     |     |     |     |     |     |     |     |     |     |     |     |
|-----|-----|-----|-----|-----|-----|-----|-----|-----|-----|-----|-----|-----|-----|-----|-----|
| Lys | Glu | Phe | Phe | His | Pro | Arg | Tyr | His | His | Arg | Glu | Phe | Arg | Phe | Asp |
|     |     |     | -145|     |     |     |     |     | -140|     |     |     |     | -135|     |

```
CTT  TCC  AAG  ATC  CCA  GAA  GGG  GAA  GCT  GTC  ACG  GCA  GCC  GAA  TTC  CGG       432
Leu  Ser  Lys  Ile  Pro  Glu  Gly  Glu  Ala  Val  Thr  Ala  Ala  Glu  Phe  Arg
          -130                      -125                     -120

ATC  TAC  AAG  GAC  TAC  ATC  CGG  GAA  CGC  TTC  GAC  AAT  GAG  ACG  TTC  CGG       480
Ile  Tyr  Lys  Asp  Tyr  Ile  Arg  Glu  Arg  Phe  Asp  Asn  Glu  Thr  Phe  Arg
     -115                      -110                     -105

ATC  AGC  GTT  TAT  CAG  GTG  CTC  CAG  GAG  CAC  TTG  GGC  AGG  GAA  TCG  GAT       528
Ile  Ser  Val  Tyr  Gln  Val  Leu  Gln  Glu  His  Leu  Gly  Arg  Glu  Ser  Asp
-100                 -95                      -90                      -85

CTC  TTC  CTG  CTC  GAC  AGC  CGT  ACC  CTC  TGG  GCC  TCG  GAG  GAG  GGC  TGG       576
Leu  Phe  Leu  Leu  Asp  Ser  Arg  Thr  Leu  Trp  Ala  Ser  Glu  Glu  Gly  Trp
               -80                      -75                      -70

CTG  GTG  TTT  GAC  ATC  ACA  GCC  ACC  AGC  AAC  CAC  TGG  GTG  GTC  AAT  CCG       624
Leu  Val  Phe  Asp  Ile  Thr  Ala  Thr  Ser  Asn  His  Trp  Val  Val  Asn  Pro
          -65                      -60                      -55

CGG  CAC  AAC  CTG  GGC  CTG  CAG  CTC  TCG  GTG  GAG  ACG  CTG  GAT  GGG  CAG       672
Arg  His  Asn  Leu  Gly  Leu  Gln  Leu  Ser  Val  Glu  Thr  Leu  Asp  Gly  Gln
          -50                      -45                      -40

AGC  ATC  AAC  CCC  AAG  TTG  GCG  GGC  CTG  ATT  GGG  CGG  CAC  GGG  CCC  CAG       720
Ser  Ile  Asn  Pro  Lys  Leu  Ala  Gly  Leu  Ile  Gly  Arg  His  Gly  Pro  Gln
     -35                      -30                      -25

AAC  AAG  CAG  CCC  TTC  ATG  GTG  GCT  TTC  TTC  AAG  GCC  ACG  GAG  GTC  CAC       768
Asn  Lys  Gln  Pro  Phe  Met  Val  Ala  Phe  Phe  Lys  Ala  Thr  Glu  Val  His
-20                      -15                      -10                      -5

TTC  CGC  AGC  ATC  CGG  TCC  ACG  GGG  AGC  AAA  CAG  CGC  AGC  CAG  AAC  CGC       816
Phe  Arg  Ser  Ile  Arg  Ser  Thr  Gly  Ser  Lys  Gln  Arg  Ser  Gln  Asn  Arg
                    1                   5                        10

TCC  AAG  ACG  CCC  AAG  AAC  CAG  GAA  GCC  CTG  CGG  ATG  GCC  AAC  GTG  GCA       864
Ser  Lys  Thr  Pro  Lys  Asn  Gln  Glu  Ala  Leu  Arg  Met  Ala  Asn  Val  Ala
          15                      20                       25

GAG  AAC  AGC  AGC  AGC  GAC  CAG  AGG  CAG  GCC  TGT  AAG  AAG  CAC  GAG  CTG       912
Glu  Asn  Ser  Ser  Ser  Asp  Gln  Arg  Gln  Ala  Cys  Lys  Lys  His  Glu  Leu
          30                      35                       40

TAT  GTC  AGC  TTC  CGA  GAC  CTG  GGC  TGG  CAG  GAC  TGG  ATC  ATC  GCG  CCT       960
Tyr  Val  Ser  Phe  Arg  Asp  Leu  Gly  Trp  Gln  Asp  Trp  Ile  Ile  Ala  Pro
45                       50                       55                       60

GAA  GGC  TAC  GCC  GCC  TAC  TAC  TGT  GAG  GGG  GAG  TGT  GCC  TTC  CCT  CTG      1008
Glu  Gly  Tyr  Ala  Ala  Tyr  Tyr  Cys  Glu  Gly  Glu  Cys  Ala  Phe  Pro  Leu
                    65                       70                       75

AAC  TCC  TAC  ATG  AAC  GCC  ACC  AAC  CAC  GCC  ATC  GTG  CAG  ACG  CTG  GTC      1056
Asn  Ser  Tyr  Met  Asn  Ala  Thr  Asn  His  Ala  Ile  Val  Gln  Thr  Leu  Val
               80                       85                       90

CAC  TTC  ATC  AAC  CCG  GAA  ACG  GTG  CCC  AAG  CCC  TGC  TGT  GCG  CCC  ACG      1104
His  Phe  Ile  Asn  Pro  Glu  Thr  Val  Pro  Lys  Pro  Cys  Cys  Ala  Pro  Thr
          95                      100                      105

CAG  CTC  AAT  GCC  ATC  TCC  GTC  CTC  TAC  TTC  GAT  GAC  AGC  TCC  AAC  GTC      1152
Gln  Leu  Asn  Ala  Ile  Ser  Val  Leu  Tyr  Phe  Asp  Asp  Ser  Ser  Asn  Val
     110                      115                      120

ATC  CTG  AAG  AAA  TAC  AGA  AAC  ATG  GTG  GTC  CGG  GCC  TGT  GGC  TGC  CAC      1200
Ile  Leu  Lys  Lys  Tyr  Arg  Asn  Met  Val  Val  Arg  Ala  Cys  Gly  Cys  His
125                      130                      135                      140

TAGCTCCTCC GAGAATTCAG ACCCTTTGGG GCCAAGTTTT TCTGGATCCT CCATTGCTC             1259
```

( 2 ) INFORMATION FOR SEQ ID NO:10:

( i ) SEQUENCE CHARACTERISTICS:
        ( A ) LENGTH: 400 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ser  Leu  Asp  Asn  Glu  Val  His  Ser  Ser  Phe  Ile  His  Arg  Arg  Leu  Arg
-260           -255                     -250                          -245

Ser  Gln  Glu  Arg  Arg  Glu  Met  Gln  Arg  Glu  Ile  Leu  Ser  Ile  Leu  Gly
               -240                     -235                          -230

Leu  Pro  His  Arg  Pro  Arg  Pro  His  Leu  Gln  Gly  Lys  His  Asn  Ser  Ala
               -225                     -220                -215

Pro  Met  Phe  Met  Leu  Asp  Leu  Tyr  Asn  Ala  Met  Ala  Val  Glu  Glu  Gly
          -210                -205                     -200

Gly  Gly  Pro  Gly  Gly  Gln  Gly  Phe  Ser  Tyr  Pro  Tyr  Lys  Ala  Val  Phe
     -195                -190                          -185

Ser  Thr  Gln  Gly  Pro  Pro  Leu  Ala  Ser  Leu  Gln  Asp  Ser  His  Phe  Leu
-180                -175                     -170                          -165

Thr  Asp  Ala  Asp  Met  Val  Met  Ser  Phe  Val  Asn  Leu  Val  Glu  His  Asp
               -160                     -155                          -150

Lys  Glu  Phe  Phe  His  Pro  Arg  Tyr  His  His  Arg  Glu  Phe  Arg  Phe  Asp
               -145                     -140                     -135

Leu  Ser  Lys  Ile  Pro  Glu  Gly  Glu  Ala  Val  Thr  Ala  Ala  Glu  Phe  Arg
          -130                     -125                     -120

Ile  Tyr  Lys  Asp  Tyr  Ile  Arg  Glu  Arg  Phe  Asp  Asn  Glu  Thr  Phe  Arg
-115                     -110                          -105

Ile  Ser  Val  Tyr  Gln  Val  Leu  Gln  Glu  His  Leu  Gly  Arg  Glu  Ser  Asp
-100                -95                      -90                          -85

Leu  Phe  Leu  Leu  Asp  Ser  Arg  Thr  Leu  Trp  Ala  Ser  Glu  Glu  Gly  Trp
               -80                      -75                     -70

Leu  Val  Phe  Asp  Ile  Thr  Ala  Thr  Ser  Asn  His  Trp  Val  Val  Asn  Pro
               -65                      -60                     -55

Arg  His  Asn  Leu  Gly  Leu  Gln  Leu  Ser  Val  Glu  Thr  Leu  Asp  Gly  Gln
          -50                      -45                      -40

Ser  Ile  Asn  Pro  Lys  Leu  Ala  Gly  Leu  Ile  Gly  Arg  His  Gly  Pro  Gln
     -35                      -30                -25

Asn  Lys  Gln  Pro  Phe  Met  Val  Ala  Phe  Phe  Lys  Ala  Thr  Glu  Val  His
-20                 -15                     -10                          -5

Phe  Arg  Ser  Ile  Arg  Ser  Thr  Gly  Ser  Lys  Gln  Arg  Ser  Gln  Asn  Arg
               1                5                          10

Ser  Lys  Thr  Pro  Lys  Asn  Gln  Glu  Ala  Leu  Arg  Met  Ala  Asn  Val  Ala
          15                20                          25

Glu  Asn  Ser  Ser  Ser  Asp  Gln  Arg  Gln  Ala  Cys  Lys  Lys  His  Glu  Leu
     30                     35                40

Tyr  Val  Ser  Phe  Arg  Asp  Leu  Gly  Trp  Gln  Asp  Trp  Ile  Ile  Ala  Pro
45                  50                     55                          60

Glu  Gly  Tyr  Ala  Ala  Tyr  Tyr  Cys  Glu  Gly  Glu  Cys  Ala  Phe  Pro  Leu
               65                     70                          75

Asn  Ser  Tyr  Met  Asn  Ala  Thr  Asn  His  Ala  Ile  Val  Gln  Thr  Leu  Val
               80                     85                          90

His  Phe  Ile  Asn  Pro  Glu  Thr  Val  Pro  Lys  Pro  Cys  Cys  Ala  Pro  Thr
          95                      100                    105

Gln  Leu  Asn  Ala  Ile  Ser  Val  Leu  Tyr  Phe  Asp  Asp  Ser  Ser  Asn  Val
     110                     115                120

Ile  Leu  Lys  Lys  Tyr  Arg  Asn  Met  Val  Val  Arg  Ala  Cys  Gly  Cys  His
125                 130                     135                         140
```